(12) United States Patent
Toner et al.

(10) Patent No.: US 7,094,601 B2
(45) Date of Patent: *Aug. 22, 2006

(54) MICROINJECTION OF CRYOPROTECTANTS FOR PRESERVATION OF CELLS

(75) Inventors: Mehmet Toner, Wellesley, MA (US); Ali Eroglu, Augusta, GA (US); Thomas Toth, Sudbury, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/749,369

(22) Filed: Dec. 31, 2003

(65) Prior Publication Data

US 2004/0248293 A1 Dec. 9, 2004

Related U.S. Application Data

(63) Continuation-in-part of application No. 09/859,105, filed on May 16, 2001, now Pat. No. 6,673,607, which is a continuation-in-part of application No. 09/798,327, filed on Mar. 2, 2001, now abandoned.

(60) Provisional application No. 60/204,877, filed on May 16, 2000.

(51) Int. Cl.
*C12N 5/00* (2006.01)
(52) U.S. Cl. ............... 435/374; 435/1.3; 435/2; 435/325; 435/366; 436/18
(58) Field of Classification Search ............... 435/374, 435/1.3, 2, 325, 366; 436/18
See application file for complete search history.

(56) References Cited

U.S. PATENT DOCUMENTS

| | | | |
|---|---|---|---|
| 4,724,206 A * | 2/1988 | Rupp et al. ............. | 435/69.1 |
| 5,182,299 A * | 1/1993 | Gullans et al. ............. | 514/460 |
| 5,496,720 A | 3/1996 | Susko-Parrish et al. .. | 435/240.2 |
| 5,654,266 A | 8/1997 | Chen et al. | |
| 5,672,502 A | 9/1997 | Birch et al. | |
| 5,827,741 A | 10/1998 | Beattie et al. ............. | 435/374 |
| 6,127,177 A | 10/2000 | Toner et al. ............. | 435/374 |
| 6,376,743 B1 | 4/2002 | Yanagimachi | |

FOREIGN PATENT DOCUMENTS

| WO | WO 97 45010 | 12/1997 |
|---|---|---|
| WO | WO 98 09514 | 3/1998 |
| WO | WO 99/31977 A1 | 7/1999 |
| WO | WO 00 15032 | 3/2000 |

OTHER PUBLICATIONS

Chen et al., "Literature Review: Supplemented Phase Diagram of the Trehalose—Water Binary Mixture," *Cryobiology* 40:277-282 (2000).

Critser et al., "The Cryobiology of Mammalian Oocytes," *Reproductive Tissue Banking* p. 329-357 (1997).

Oktay et al., "Cryopreservation of Immature Human Oocytes and Ovarian Tissue: An Emerging Technology?," *Fertility And Sterility* 69(1):1-7 (1998).

Shanina et al., "A Comparision of a Sucrose-based Solution with Other Preservation Media for Cold Storage of Isolated Hepatocytes," *Cryobiology* 41:315-318 (2000).

Beattie et al., "Trehalose: A cryoprotectant that enhances recovery and preserves function of human pancreatic islets after long-term storage," *Diabetes* 46:519-523 (1997).

Donnamaria et al., "Interaction of water with α,α-trehalose in solution: molecular dynamics simulation approach," *Chem. Soc. Faraday Trans.* 90(18):2731-2735 (1994).

Eroglu et al., "Intercellular trehalose improves the survival of cryopreserved mammalian cells," *Nature Biotechnology* 18:163-167 (2000).

Guo et al., "Trehalose expression confers desicccation tolerance on human cells," *Nature Biotechnology* 18:168-171 (2000).

Janik et al., "Overcoming a permeability barrier by microinjecting cryoprotectants into zebrafish embryos (*Brachydanio rerio*)," *Cryobiology* 41:25-34 (2000).

Knight et al., "Microinjection of $^{14}$C-sucrose and other tracers into isolated phloem strands of heracleum," *Can. J. Bot.* 52:1491-1499 (1974).

Hagedom et al., "Magnetic resonance microscopy and spectroscopy reveal kinetics of cryoprotectant permeation in a multicompartmental biological system," *Proc. Natl. Acad. Sci. U.S.A.* 93:7454-7459 (1996).

Hagedom et al., "New approaches for studying the permeability of fish embryos: Toward successful cryopreservation," *Cryobiology* 34:335-347 (1997).

Levine et al., "Thermomechanical properties of small-carbohydrate-water glasses and 'rubbers'," *J. Chem. Soc., Faraday Trans.*, 84(8):2619-2633 (1988).

Marchase et al., "Glucose phosphotransferase and intracellular trafficking," *Molecular and Cellular Biochemistry* 72:101-107 (1986).

Paynter et al., "Permeability characteristics of human oocytes in the presence of the cryoprotectant dimethylsulphoxide," *Human Reproduction* 14(9):2338-2342 (1999).

(Continued)

*Primary Examiner*—Leon B. Lankford, Jr.
(74) *Attorney, Agent, or Firm*—Clark & Elbing LLP

(57) ABSTRACT

A preservation method for biological material having cell membranes includes microinjecting the cells with sugar; preparing the cells for storage; storing the biological material; and recovering the stored biological material from storage. The invention also features a method of culturing a cell in vitro using a hypertonic medium. Carbohydrate sugars such as trehalose, sucrose, fructose, dextran, and raffinose, may be used as bio-protective agents or in the culture medium.

26 Claims, 24 Drawing Sheets

OTHER PUBLICATIONS

Rayos et al., "Quick freezing of unfertilized mouse oocytes using ethylene glycol with sucrose of trehalose," *Journal of Reproduction and Fertility* 100:123-129 (1994).

Russo et al., "Reversible permeabilization of plasma membranes with an engineered switchable pore," *Nature Biotechnology* 15:278-282 (1997).

Toner et al "Cryomicroscopic Analysis of Intracellular Ice Formation during Freezing of Mouse Oocytes Without Cryoadditives," Cryobiology 28: 55-71 (1991).

Oda et al., "Osmotic Shock of Fertilized Mouse Ova," *Journal of Reproduction and Fertility, UK* 95:737-747 (1992).

Van Os et al., "Volumetric Behavior and Survival of Mouse Zygotes and Embryos in Hyperosmotic Media," *Human Reproduction* 1:95-98 (1986).

Bell et al, "Effects of Constrast Media on Calcium Transients and Motion in Cultured Ventricular Cells, " *Investigavtive Radiology* 23:842-846 (1988).

\* cited by examiner

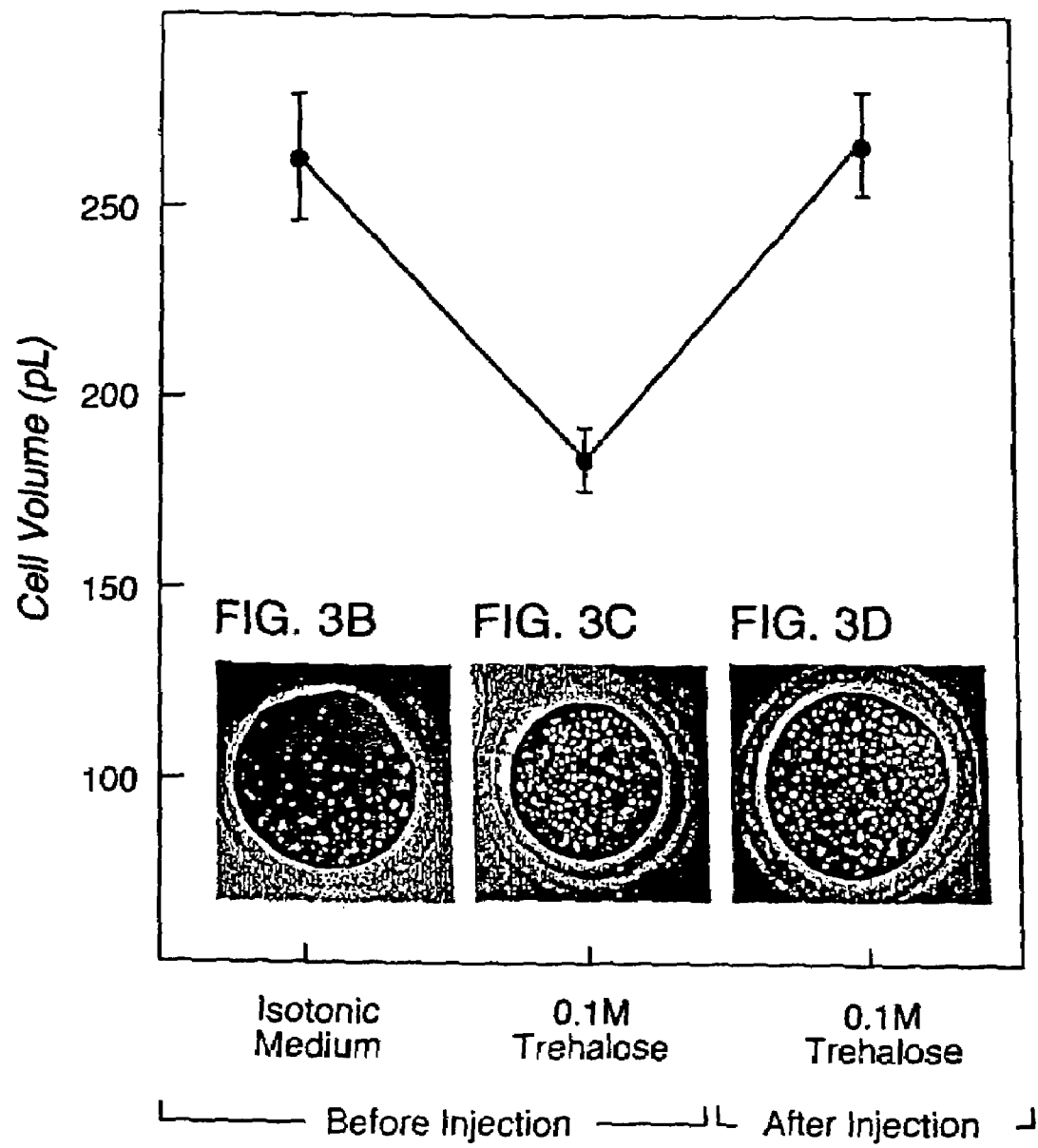

Isotonic Medium Before Injection 0.15M Trehalose Before Injection 0.15M Trehalose During Injection 0.15M Trehalose After Injection

FIG. 7

| Component | HTF | Modified HTF Isotonic | Modified HTF Hypertonic |
|---|---|---|---|
| NaCl (mM) | 101.60 | ↓ 95.00 | 106.70 |
| KCl (mM) | 4.69 | ↑ 4.78 | 5.37 |
| $KH_2PO_4$ (mM) | 0.37 | ↑ 0.38 | 0.43 |
| $MgSO_4 \cdot 7H_2O$ (mM) | 0.20 | 0.20 | 0.22 |
| $NaHCO_3$ (mM) | 25.00 | ↓ 25.00 | 28.07 |
| $CaCl_2 \cdot 2H_2O$ (mM) | 2.04 | 2.00 | 2.25 |
| Lactate (mM) | 21.40 | ↓ 20.00 | 22.46 |
| Pyruvate (mM) | 0.33 | 0.33 | 0.37 |
| D-Glucose (mM) | 2.78 | 2.78 | 3.12 |
| L-Glutamine (mM) | --- | ↑ 1.00 | 1.12 |
| BSA (mg/ml) | 4 | 4.00 | 4.00 |
| EDTA | --- | ↑ 0.01 | 0.01 |
| Essential amino acids | --- | ↑ 0.5x | 0.5x |
| Non-essential amino acids | --- | ↑ 0.5x | 0.5x |
| Phenol red (% w/v) | 0.01 | 0.001 | 0.001 |
| Gentamicin (mg/ml) | 50.00 | 50.00 | 50.00 |
| Osmolarity (mosm) | 285.00 | 285.00 | 320.00 |

FIG. 8

| Culture Condition | No. of Experiments | No. of Inseminated Oocytes | Percent Two-cell | Percent Blastocyst |
|---|---|---|---|---|
| Modified HTF, isotonic | 5 | 58 | 90% (52/58) | 87% (51/58) |
| Modified HTF, hypertonic | 9 | 234 | 90% (211/234) | 86% (202/234) |
| $[Tre]^{ln} = 0.07M$ | 3 | 32 | 78% (25/32) | 66% (21/32) |
| $[Tre]^{ln} = 0.15M$ | 5 | 69 | 67% (46/69) | 29% (20/69) |

FIG. 14

| Solute | $M_w$ | $T_{g'}$ °C |
|---|---|---|
| erythrose | 120.1 | -50 |
| threose | 120.1 | -45.5 |
| erythritol | 122.1 | -53.5 |
| thyminose(deoxyribose) | 134.1 | -52 |
| ribulose | 150.1 | -50 |
| xylose | 150.1 | -48 |
| arabinose | 150.1 | -47.5 |
| lyxose | 150.1 | -47.5 |
| ribose | 150.1 | -47 |
| arabitol | 152.1 | -47 |
| ribitol | 152.1 | -47 |
| xylitol | 152.1 | -46.5 |
| methyl riboside | 164.2 | -53 |
| methyl xyloside | 164.2 | -49 |
| quinovose (deoxyglucose) | 164.2 | -43.5 |
| fucose (deoxygalactase) | 164.2 | -43 |
| rhamnose (deoxymannose) | 164.2 | -43 |
| talose | 180.2 | -44 |
| idose | 180.2 | -44 |
| psicose | 180.2 | -44 |
| altrose | 180.2 | -43.5 |
| glucose | 180.2 | -43 |
| gulose | 180.2 | -42.5 |
| fructose | 180.2 | -42 |
| galactose | 180.2 | -41.5 |

FIG. 14 CONT.

| Solute | $M_w$ | $T_g$, °C |
|---|---|---|
| allose | 180.2 | -41.5 |
| sorbose | 180.2 | -41 |
| mannose | 180.2 | -41 |
| tagatose | 180.2 | -40.5 |
| inositol | 180.2 | -35.5 |
| mannitol | 182.2 | -40 |
| galactitol | 182.2 | -39 |
| sorbitol | 182.2 | -43.5 |
| 2-O-methyl fructoside | 194.2 | -51.5 |
| β-1-O-methyl glucoside | 194.2 | -47 |
| 3-O-methyl glucoside | 194.2 | -45.5 |
| 6-O-methyl galactoside | 194.2 | -45.5 |
| α-1-O-methyl glucoside | 194.2 | -44.5 |
| 1-O-methyl galactoside | 194.2 | -44.5 |
| 1-O-methyl mannoside | 194.2 | -43.5 |
| 1-O-ethyl glucoside | 208.2 | -46.5 |
| 2-O-ethyl fructoside | 208.2 | -46.5 |
| 1-O-ethyl galactoside | 208.2 | -45 |
| 1-O-ethyl mannoside | 208.2 | -43.5 |
| glucoheptose | 210.2 | -37.5 |
| mannoheptulose | 210.2 | -36.5 |
| glucoheptulose | 210.2 | -36.5 |
| perseitol (mannoheptitol) | 212.2 | -32.5 |
| 1-O-propyl glucoside | 222.2 | -43 |
| 1-O-propyl galactoside | 222.2 | -42 |

FIG. 14 CONT.

| Solute | $M_w$ | $T_g$, °C |
|---|---|---|
| 1-O-propyl mannoside | 222.2 | -40.5 |
| 2,3,4,6-O-methyl glucoside | 236.2 | -45.5 |
| isomaltulose (palatinose) | 342.3 | -35.5 |
| nigerose | 342.3 | -35.5 |
| cellobiulose | 342.3 | -32.5 |
| isomaltose | 342.3 | -32.5 |
| sucrose | 342.3 | -32 |
| gentiobiose | 342.3 | -31.5 |
| laminaribiose | 342.3 | -31.5 |
| turanose | 342.3 | -31 |
| mannobiose | 342.3 | -30.5 |
| melibiose | 342.3 | -30.5 |
| lactulose | 342.3 | -30 |
| maltose | 342.3 | -29.5 |
| maltulose | 342.3 | -29.5 |
| trehalose | 342.3 | -29.5 |
| cellobiose | 342.3 | -29 |
| lactose | 342.3 | -28 |
| maltitol | 344.3 | -34.5 |
| isomaltotriose | 504.5 | -30.5 |
| panose | 504.5 | -28 |
| raffinose | 504.5 | -26.5 |
| maltotriose | 504.5 | -23.5 |
| nystose | 666.6 | -26.5 |
| stachyose | 666.6 | -23.5 |

FIG. 14 CONT.

| Solute | $M_w$ | $T_g$ °C |
|---|---|---|
| maltotetraose | 666.6 | -19.5 |
| maltopentaose | 828.9 | -16.5 |
| α-cyclodextrin | 972.9 | -9 |
| maltohexaose | 990.9 | -14.5 |
| maltoheptaose | 1153.0 | -13.5 |

FIG. 20

| Component | Hyper 320 | Hyper 340 | Hyper 360 |
|---|---|---|---|
| NaCl (mM) | 107.02 | 115.90 | 123.50 |
| KCl (mM) | 5.38 | 5.83 | 6.21 |
| $KH_2PO_4$ (mM) | 0.43 | 0.46 | 0.49 |
| $MgSO_4 \cdot 7H_2O$ (mM) | 0.23 | 0.24 | 0.26 |
| $NaHCO_3$ (mM) | 28.16 | 30.50 | 32.50 |
| $CaCl_2 \cdot 2H_2O$ (mM) | 2.25 | 2.44 | 2.60 |
| Lactate (mM) | 22.53 | 24.40 | 26.00 |
| Pyruvate (mM) | 0.37 | 0.40 | 0.43 |
| D-Glucose (mM) | 3.13 | 3.39 | 3.61 |
| L-Glutamine (mM) | 1.13 | 1.22 | 1.30 |
| EDTA (mM) | 0.01 | 0.01 | 0.01 |
| Phenol red (mM) | 0.03 | 0.03 | 0.03 |
| BSA (mg/mL) | 4.00 | 4.00 | 4.00 |
| Gentamicin (mg/ml) | 50.00 | 50.00 | 50.00 |
| Essential amino acids[i] (mL/L) | 10.00 | 10.00 | 10.00 |
| Non-essential amino acids[ii] (mL/L) | 5.00 | 5.00 | 5.00 |
| Osmolality | 320 | 340 | 360 |

[i] [50X Solution, Gibco]
[ii] [100X Solution, Gibco]

MICROINJECTION OF CRYOPROTECTANTS FOR PRESERVATION OF CELLS

CROSS-REFERENCE TO RELATED APPLICATIONS

This application is a continuation-in-part of Ser. No. 09/859,105, filed May 16, 2001 now U.S. Pat. No. 6,673,607, which is a continuation-in-part of Ser. No. 09/798,327, filed Mar. 2, 2001, now abandoned, which claims priority from U.S. Provisional Application No. 60/204,877, filed May 16, 2000, now abandoned, all of which are hereby incorporated by reference.

FIELD OF THE INVENTION

The present invention relates to the preservation of biological tissue using microinjection of intracellular protective agents containing sugar to preserve cells by freezing and/or drying.

BACKGROUND OF THE INVENTION

In recent years, chemotherapy and radiation therapy of patients with cancer has been increasingly successful and sustained remissions have been achieved. However, the chronic side effects of these therapies to the reproductive systems of long-term survivors is of particular concern. These effects for women include depletion of ovarian germ cells and sterility. Due to the potential loss of future fertility of those exposed to cancer therapy, a need for oocyte banking has developed. Oocyte freezing, when combined with in vitro fertilization, may be beneficial to women desiring future fertility who are anticipating loss of gonadal function from extirpative therapy, radiation, or chemotherapy. Oocyte freezing may also provide a possible alternative to human embryo freezing, thus avoiding many of the legal and ethical problems encountered in embryo freezing.

The first successful cryopreservation of human embryos was achieved in 1983 and embryo freezing is now a routine procedure. In contrast, very limited success has been reported with cryopreservation of human oocytes. Only five successful pregnancies have been reported with more than 1500 cryopreserved oocytes. Therefore, the current methods of freezing are still considered experimental and novel approaches are needed to overcome the difficulty encountered by cryopreservation of the human oocyte.

Traditional cryopreservation techniques include penetrating cryoprotectants at concentrations of 1 to 2 M with, for example, dimethyl sulfoxide (DMSO), glycerol, or ethylene glycol, followed by a slow freezing rate (0.3 to 0.5° C./min). Typically, oocytes are damaged due to long-term exposure to deleterious freezing conditions, including excessive dehydration and high electrolyte concentrations. An alternative approach, called vitrification (i.e., formation of glassy material without crystallization of ice, uses high concentrations of cryoprotectant mixtures (6 to 8 M) followed by rapid cooling in order to avoid the lethal effects of freezing on oocytes.

Though an attractive alternative, vitrification procedures suffer from the toxic and osmotic effects of high cryoprotectant concentration on sensitive cells. Neither of these two approaches (slow freeze-thaw and rapid vitrification) has resulted in a reliably successful outcome for cryopreservation of human oocytes. Thus, there is a need for a reliable technique for human oocyte storage. In order to provide the preservation of mammalian cells necessary for application of living cells as a therapeutic tool in clinical medical care, new protocols for preserving living nucleated cells using low levels of non-toxic preservation agents and having simple procedures applicable to a variety of cells must be developed.

SUMMARY OF THE INVENTION

The purpose of the present invention is to culture a cell in vitro in a hypertonic medium that maintains the viability of the cell. The in vitro culturing methods can be used subsequent to storage and recovery of living cells. This method has the advantage of allowing any mammalian cell to be maintained in culture until it is needed under conditions that cause minimal, if any, adverse side-effects in the cell.

Thus, the invention, in some embodiments, provides a method for culturing a living cell, preferably an oocyte or an embryo. Other preferred cells that may be preserved include differentiated cells, such as epithelial cells, neural cells, epidermal cells, keratinocytes, hematopoietic cells, melanocytes, chondrocytes, B-cells, T-cells, erythrocytes, macrophages, monocytes, fibroblasts, or muscle cells; and undifferentiated cells, such as embryonic, mesenchymal, or adult stem cells. In one preferred embodiment, the differentiated cells remain differentiated after they are recovered from a frozen or dried state, and the undifferentiated cells remain undifferentiated after they are recovered. The cells can be haploid (DNA content of n; where "n" is the number of chromosomes found in the normal haploid chromosomes set of a mammal of a particular genus or species), diploid (2n), or tetraploid (4n). Other cells include those from the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus. The cells may be from a human or non-human mammal, such as a monkey, ape, cow, sheep, big-horn sheep, goat, buffalo, antelope, oxen, horse, donkey, mule, deer, elk, caribou, water buffalo, camel, llama, alpaca, rabbit, pig, mouse, rat, guinea pig, hamster, dog, or cat.

The method of the invention involves incubating the cell in vitro in a hypertonic medium having an osmolarity greater than 300, 310, 320, 330, 340, 350, 360, 370, 380, or more mosm. In preferred embodiments of the invention, the hypertonic medium has an osmolarity of 320 mosm, 340 mosm, or 360 mosm. Preferably, the medium includes one or more of the components listed in FIG. 7 or FIG. 20 or one or more cryopreservation agents described herein. Preferably, the medium contains nutrients such as amino acids, sugars, lactate, or pyruvate. The hypertonic medium may also include low levels, less than or equal to about 6, 5, 4, 3, 2, or 1 M, 0.4 M, 0.3M, 0.2M, 0.1M, 0.05M, or 0.01 M of preservation agent, such as a sugar or a conventional cryoprotectant, or a combination of both. Preferred sugars include sucrose, trehalose, fructose, dextran, and raffinose. This medium may be used to culture any mammalian cell, including the preferred cells listed above. In various preferred embodiments, this media is used to culture cells before, during, or after cryopreservation.

By "culturing" is meant cultivating or growing a cell in a specially prepared nutrient medium. The "cultured" cell can be a cell that is dividing, expanding, resting or differentiating. The cells can be cultured in suspension, as an adherent monolayers, or as a semi-adherent where there is a mixed population of adherent and suspended cells.

By "embryo" is meant a developing cell mass that has not implanted into the uterine membrane of a maternal host.

Hence, the term "embryo" may refer to a fertilized oocyte, a pre-blastocyst stage developing cell mass, or any other developing cell mass that is at a stage of development prior to implantation into the uterine membrane of a maternal host and prior to formation of a genital ridge. An embryo may represent multiple stages of cell development. For example, a one cell embryo can be referred to as a zygote; a solid spherical mass of cells resulting from a cleaved embryo can be referred to as a morula, and an embryo having a blastocoel can be referred to as a blastocyst.

By "fetus" or "fetal" is meant a developing cell mass that has implanted into the uterine membrane of a maternal host. A fetus may have defining features such as a genital ridge which is easily identified by a person of ordinary skill in the art.

By "osmolarity" is meant the concentration of osmotically active particles expressed in terms of osmoles or milliosmoles of solute per liter of solution. By "osmolality" is meant the concentration of osmotically active particles expressed in terms of osmoles or milliosmoles of solute per 1000 grams of solvent.

BRIEF DESCRIPTION OF THE DRAWINGS

The invention will be more fully understood from the following detailed description taken in conjunction with the accompanying drawings, in which:

FIG. 3A is a graph showing the volume of mouse oocytes in isotonic DMEM/F-12 medium prior to microinjection, DMEM/F-12 with 0.1 M extracellular trehalose (hypertonic medium) prior to microinjection, and DMEM/F-12 with 0.1 M extracellular trehalose (hypertonic medium) after microinjection of 0.1 M trehalose. FIGS. 3B–3D are phase-contrast microscopy pictures of the oocytes under each of the three conditions listed above.

FIG. 7 is a table listing the components of HTF, modified isotonic HTF, and modified hypertonic HTF media.

FIG. 8 is a table listing the percentage of metaphase II mouse oocytes with or without intracellular trehalose that were fertilized and developed into blastocysts while being cultured in modified HTF, isotonic or modified HTF, hypertonic media.

FIG. 14 is a table listing the molecular weight and glass transition temperature for sugars with a glass transition temperature greater than −55° C. (Levine and Slade, J. Chem. Soc., Faraday Trans. 1, 84:2619–2633, 1988). Many of these sugars are commercially available from sources such as Sigma and British Sugar.

FIG. 20 is a table listing the components of modified hypertonic HTF media at different osmolalities.

DETAILED DESCRIPTION

Figure 1:
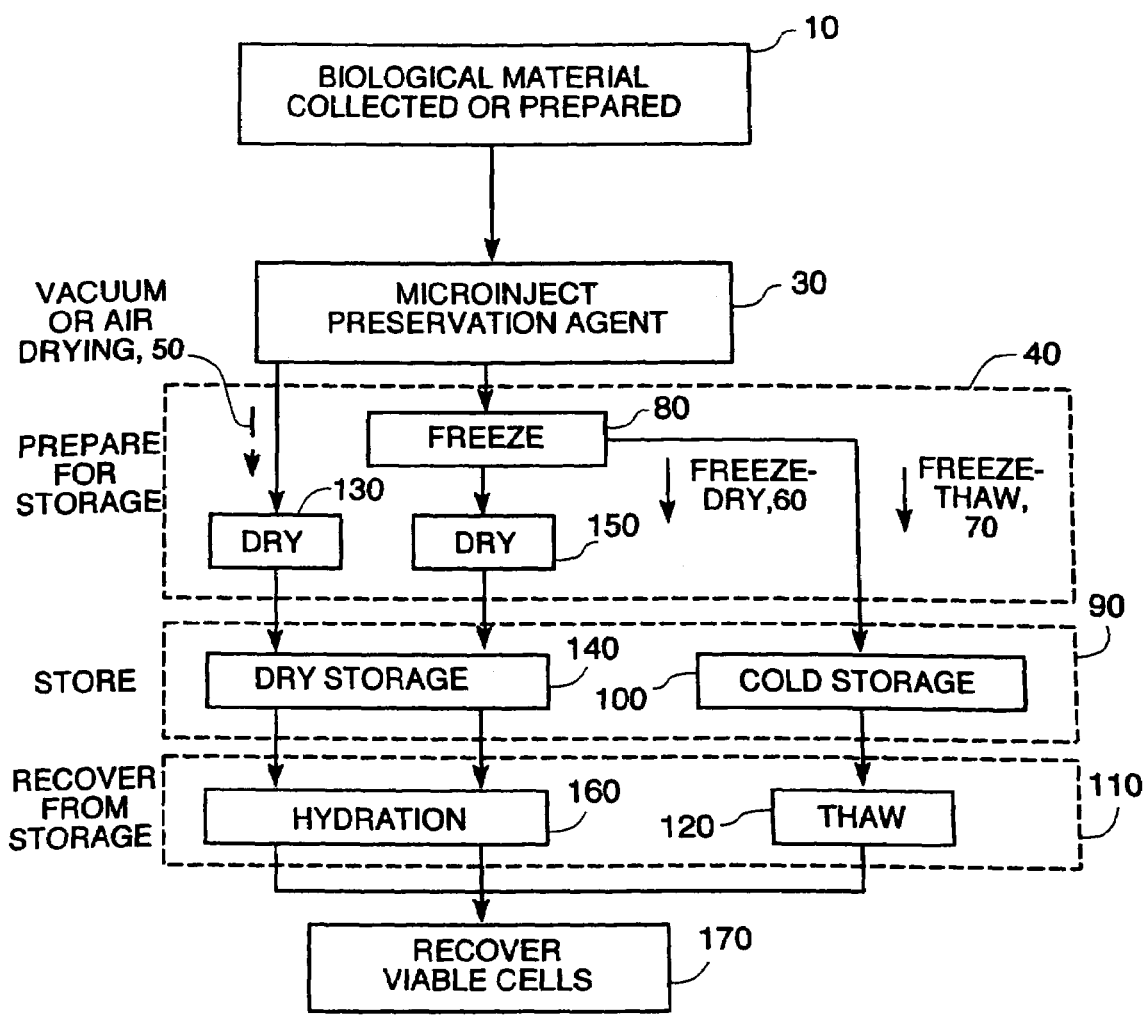
FIG. 1 is a flow chart showing steps in the method of the invention. Each of the numbers (10–170) is used parenthetically in the detailed description below to reference the specific step in the flow chart.
Figure 2:
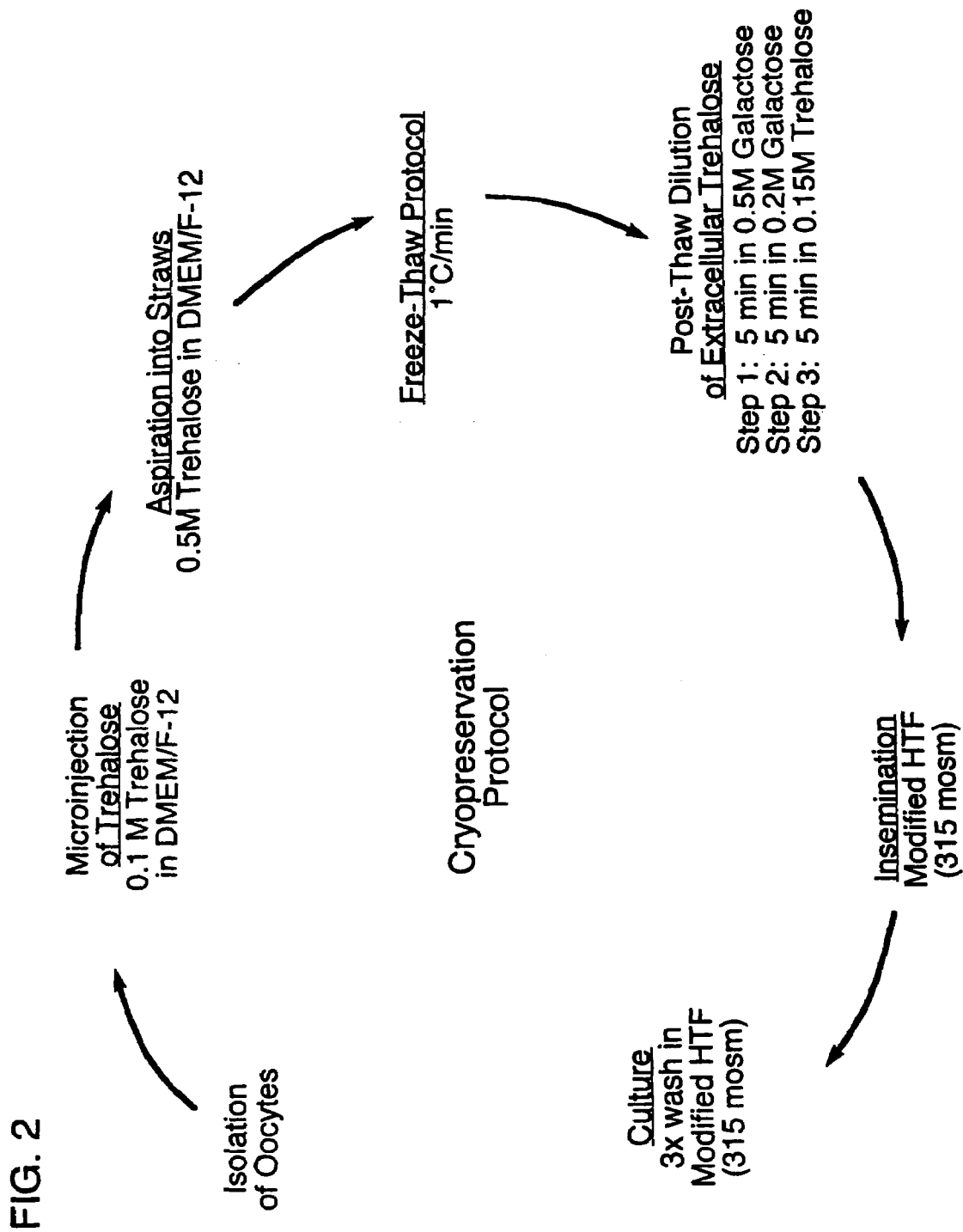
FIG. 2 is a schematic flow diagram listing one embodiment of the cyropreservation protocol of the present invention. This protocol may be modified by one skilled in the art for the preservation of other cells using other cyropreservation agents, cooling rates, dilution steps, and media.
Figure 4A:
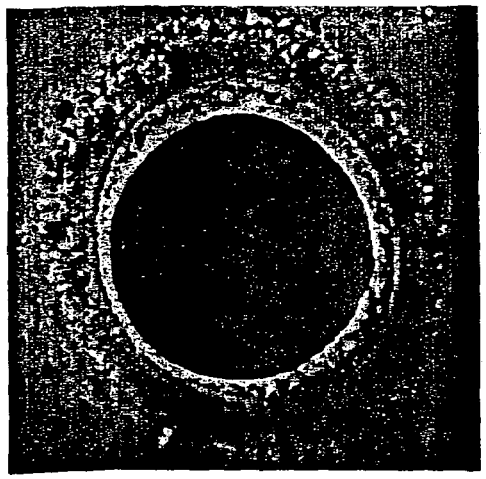
FIGS. 4A–4D are bright-field microscopy pictures of human oocytes in isotonic DMEM/F-12 medium prior to microinjection, DMEM/F-12 with 0.15 M extracellular trehalose (hypertonic medium) prior to microinjection, DMEM/F-12 with 0.15 M extracellular trehalose (hypertonic medium) during microinjection, and DMEM/F-12 with 0.15 M extracellular trehalose (hypertonic medium) after microinjection of 0.15 M trehalose, respectively.
Figure 4B:
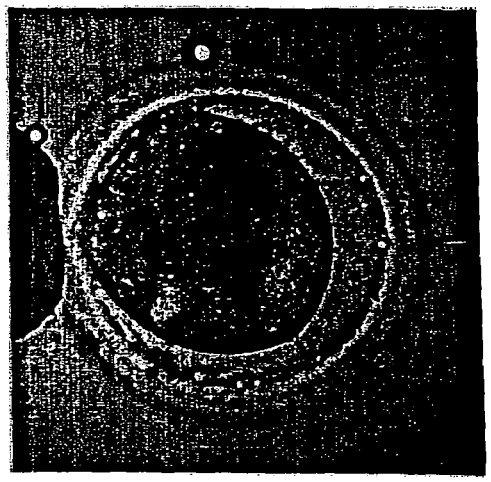
Figure 4C:
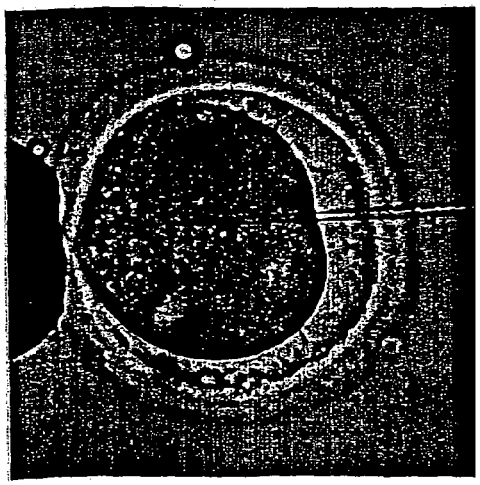
Figure 4D:
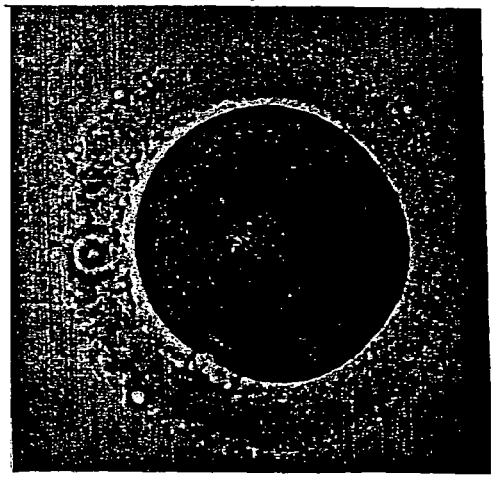

A method for preserving biological tissue of the invention, illustrated in FIG. 1 and FIG. 2, starts with the selection or isolation of the cells or tissue to be preserved (10). While the method of the invention may be used for preservation of any biological material having lipid membranes, it is most useful for preservation of living nucleated cells and, in particular, otherwise difficult to preserve mammalian cells such as oocytes.

Oocytes can be obtained by isolating oviducts and/or ovaries and releasing the oocytes. The oocytes are transferred to hyaluronidase, an enzyme that breaks down extra cells. The oocytes are then washed twice in HEPES-buffered Dulbecco's Modified Eagle Medium/Nutrient F-12 (DMEM/F-12) mixture (Gibco) and BSA (bovine serum albumin). Oocytes are then transferred to modified, isotonic HTF covered with embryo-tested mineral oil (Sigma), or any other suitable medium. The DMEM/F12 media is preferably supplemented with 4 mg/mL BSA. If desired, the oocytes may also be incubated with extracellular sugar at the same concentration as the amount planned for microinjection. For example, to inject 0.1 M sugar, oocytes may be equilibrated in DMEM/F-12 with 0.1 M sugar. As illustrated in FIGSA. 3A–3C, the hyperosmoticity of the external DMEM/F-12+sugar solution causes mouse oocytes to shrink. This decrease in cell volume may be quantitated by visually measuring the diameter of the cells using phase-contrast microscopy. The decrease in cell volume facilitates the determination of how much sugar is subsequently microinjected into the oocytes. For example, the swelling of cells during microinjection to their initial isotonic volume (i.e., the cell volume prior to equilibration with external sugar) indicates that the concentration of injected sugar is close to that of the extracelluar sugar concentration (FIGS. 3A–3D). Similar results obtained when human oocytes were incubated in 0.15 M extracellular trehalose, causing their volume to decrease, and then injected with trehalose until the volume of the oocytes returned to their initial volume in isotonic media, indicated that 0.15 M trehalose had been injected (FIGS. 4A–D). Alternatively, the oocytes may be optionally equilibrated with any other substantially non-permeable solute, such a NaCl, to decrease their cell volume prior to microinjection. This initial decrease in cell volume may result in a smaller final volume of the microinjected oocytes compared to oocytes not incubated in a hypertonic media prior to microinjection. This smaller final volume may minimize any potential adverse effect from the swelling of the oocytes. This general procedure for the preparation of cells for microinjection may also be used for other cell types.

The target cells are then microinjected (30) with a biopreservation agent. Microinjection equipment and procedures are well characterized in the art and microinjection equipment known for use in injecting small molecules into cells may be used with the invention. In an exemplary microinjection step, oocytes can be microinjected at a pressure of 10 psi for 30 milliseconds. Another example of a standard microinjection technique is the method described by Nakayama and Yanagimachi (Nature Biotech. 16:639–642, 1998).

For the microinjection of preservation agents, injection pipettes were manufactured from 1-mm borosilicate thin-wall (B 100-75-10, Sutter, Novato, Calif.) glass capillaries. First, the pipettes were pulled using a horizontal micropipette puller (Model P-97, Sutter) such that they had a long shank (~1.3 cm). To obtain a sharp tip with an inside diameter of approximately 0.5 μm, the injection pipettes were beveled at an angle of 40° on a modified Sutter micropipette beveler (BV-10, Sutter) allowing variable rotation speed of the abrasive plate.

Figure 5:
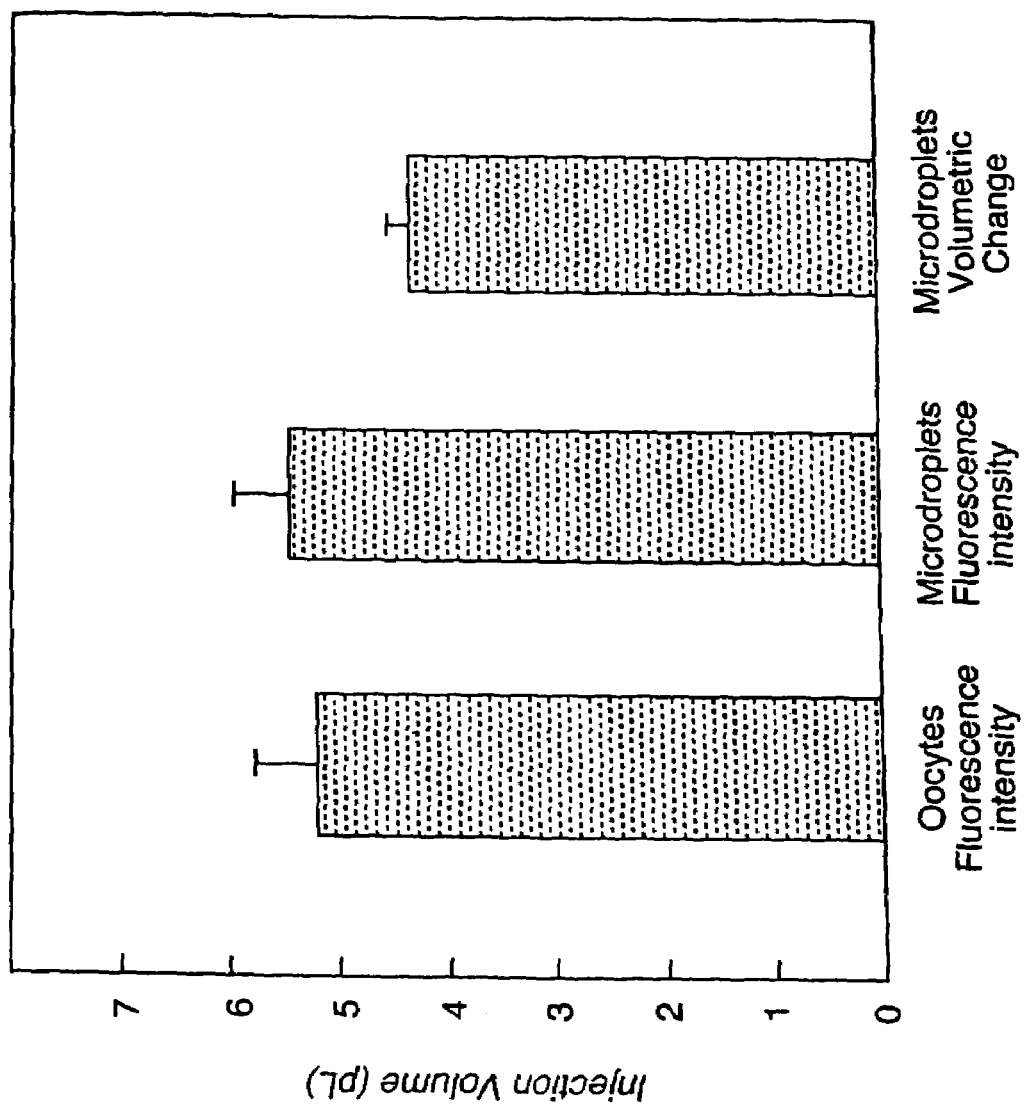
FIG. 5 is a bar graph illustrating the calibration of a micropipette used for microinjection of a cyropreservation agent of the invention.
Figure 16:
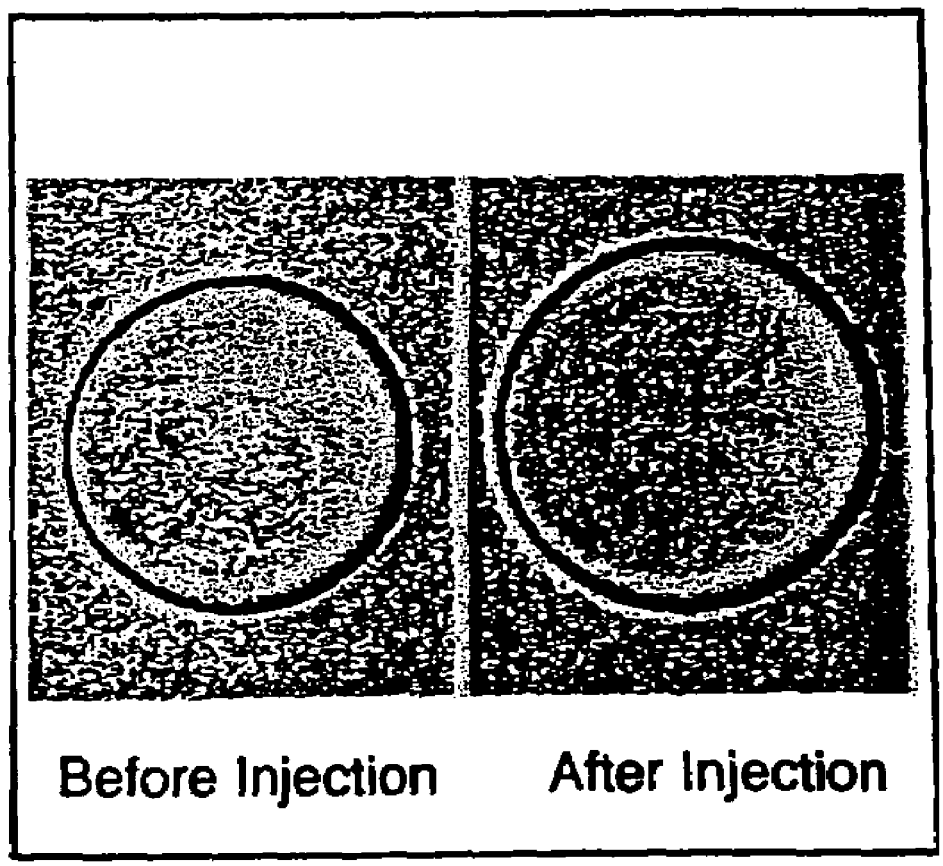
FIG. 16 is a bright-field microscopy picture of a microdroplet before and after injection of trehalose solution.
Figure 17:
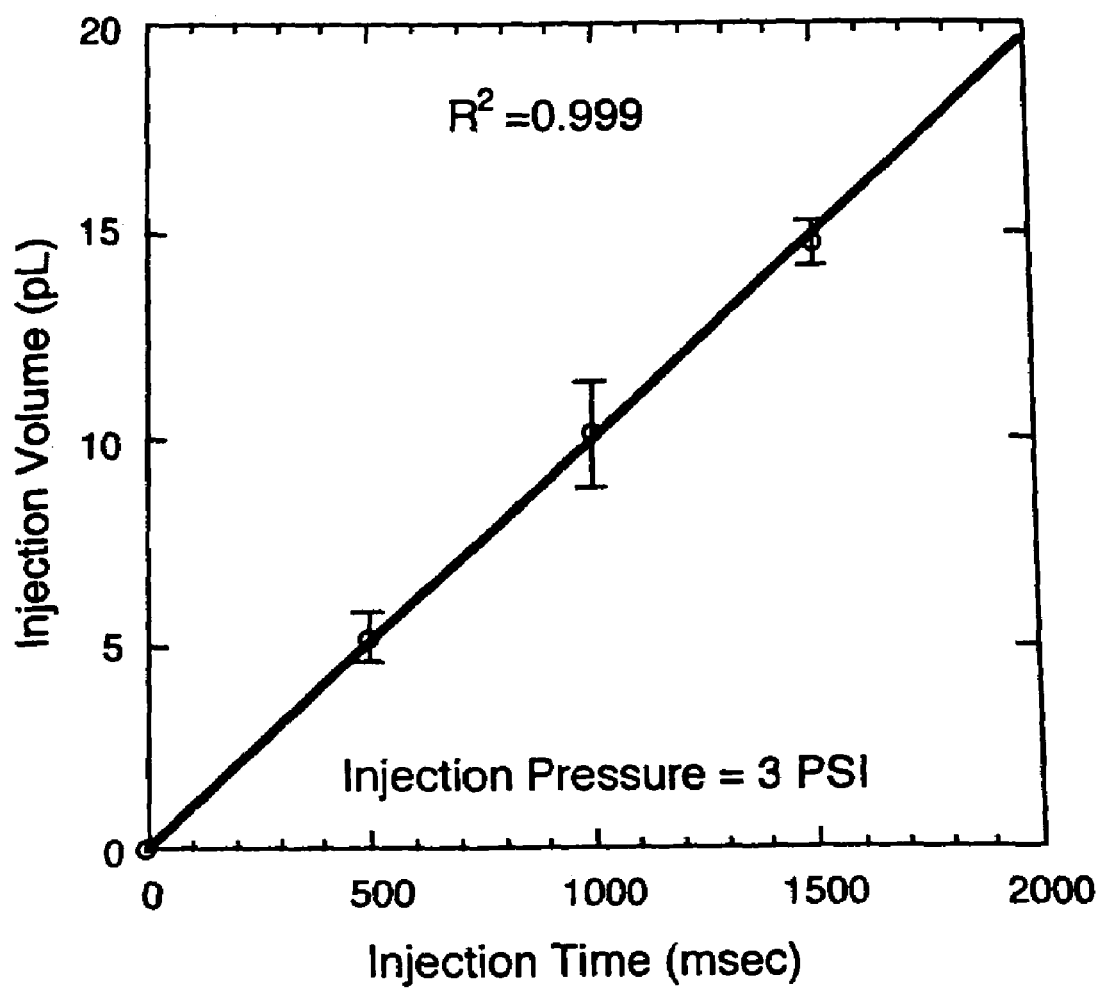
FIG. 17 is a graph of the injection volume (pL) for various injection times (msec) at an injection pressure of 3 PSI for a microdroplet injected with trehalose solution.

If desired, the micropipette used for microinjection of the cyropreservation agent may be calibrated prior to injection (FIG. 5). For this calibration, a microdroplet of DMEM/F-12 medium suspended in a solution of dimethypolysilaxene was injected with a sugar solution of interest. Preferably, the microdroplet has a similar size as that of the cells that will be microinjected. For example, microdroplets with a diameter of 70–100 were used to calibrate a micropipette for the microinjection of oocytes. To measure different injection volumes from a given injection pipette, several microdroplets were injected by varying injection time and pressure. Images of each microdroplet were taken using bright-field microscopy before and after injection to calculate the increase in the volume of the droplets and thus the injection volume (FIG. 16). Because the microdroplets are almost perfect spheres, the droplet volumes were reliably calculated using the diameter of the droplets. For example, the volume may be calculated from a cross-sectional image using the formula $V=0.75226 (A)^{3/2}$, where A is the cross sectional area of the microdroplet. In order to determine very small injection volumes, ten consecutive microinjections into a microdroplet were used to produce a measurable volume. This total increase in volume was divided by ten to obtain the average volume per injection. For a given injection pipette, the injection pressure and the pulse duration (i.e., the duration of injection) were two major factors that effected the injection volumes. To calibrate the injection pipettes, the injection pressure was fixed at an appropriate value, and the pulse duration was varied. The injection volume varied linearly as a function of increasing pulse duration (FIG. 17). By varying the pulse duration and collecting enough data points, a slope was generated for a given injection pipette. This slope was particularly useful for choosing different injection volumes for the actual experiments. After calibration, the micropipettes were washed with distilled water by aspirating and blowing out the water. Next, any remaining dimethylpolysilaxene was removed by immersing the micropipettes into methylene chloride (Fisher, Pittsburgh, Pa.) and then washing the micropipettes with distilled water and pure ethanol. The micropipettes were further prepared for actual cell microinjection by exposing them to vapors of hexamethyldisilazene in a desiccator for several hours to prevent attachment of cell debris to the pipette.

Figure 18:
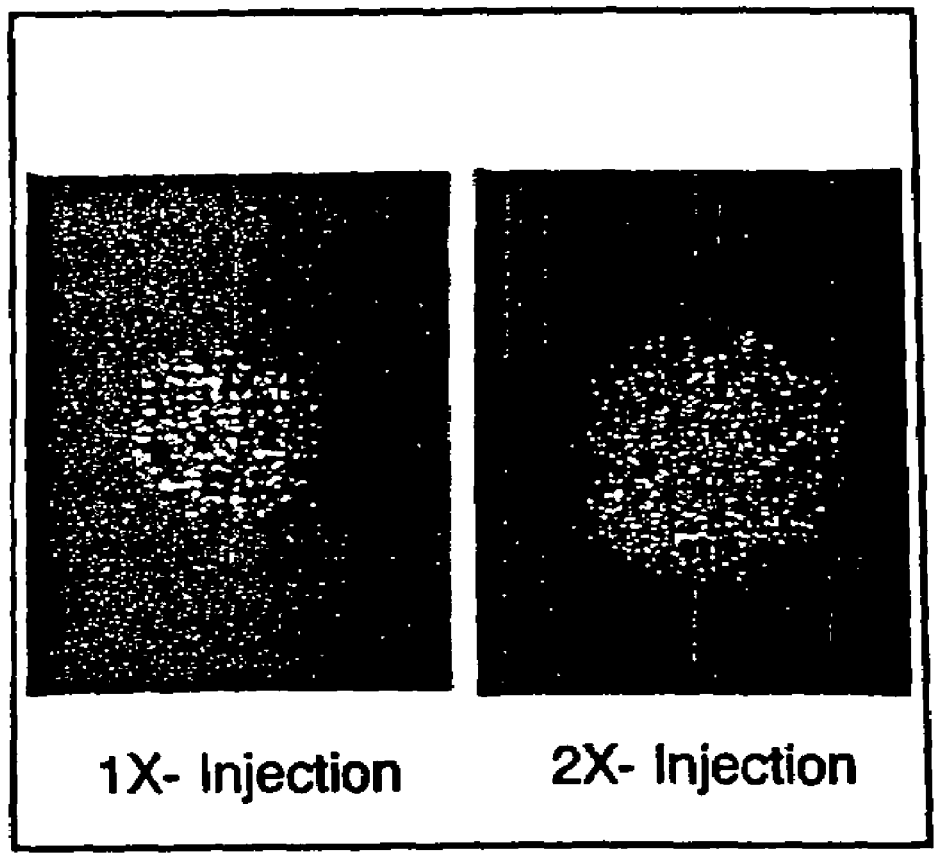
FIG. 18 is a series of pictures of fluorescent images of oocytes that have been injected once ("1×") or twice ("2×") with the fluorescent sugar, oregon-green labeled dextran, as described herein.
Figure 19:
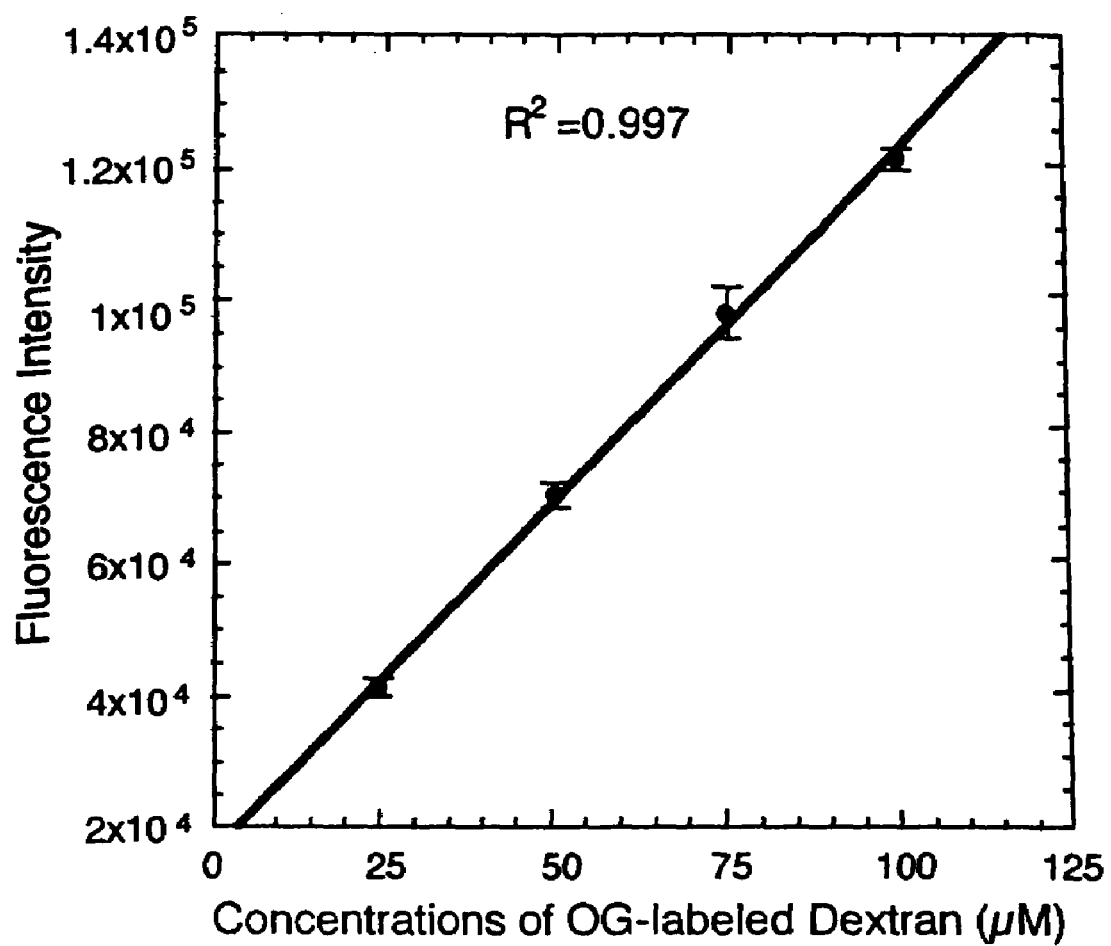
FIG. 19 is a graph of a standard curve of fluorescent intensity for different concentrations of the OG-labeled dextran within the microdroplets.

The accuracy of this pre-calibration technique was confirmed using an alternative technique which involved microinjection of Oregon-Green- (OC) labeled dextran (Molecular Probes, Eugene, Oreg.) into oocytes as well as microdroplets. For microinjection of oocytes, 80 μL of DMEM/F12 medium and 20 μL of OG-labeled dextran solution (1 mM) prepared in 10 mM Tris (pH 7.4) were placed in a 60×10-mm Falcon plastic culture dish (Fisher) and covered with the mineral oil. Next, oocytes were transferred to the injection drop. Before microinjection, both the holding and the injection pipettes were bent such that their tip portion was horizontal to the focal plane. The holding pipette was filled with the medium and connected to a manual syringe (Sutter) via plastic tubing filled with mineral oil. Similarly, the injection pipette was connected to the Pico Injector via plastic tubing, and the dextran solution was aspirated into the injection pipette. Later, a slight positive balance pressure was applied to the system throughout the microinjection procedure to prevent suction of the outside medium into the injection pipette. During microinjection, an oocyte with the spindle at the 12 or 6 o'clock position was held on the tip of the holding pipette by applying suction via a manual syringe while the injection pipette was inserted into the oocyte from the opposite side. A piezo injector (PM-20, Stoelting) was used to facilitate penetration of the injection pipette by a sudden thrusting movement. Next, the OG-labeled dextran solution was injected into the oocyte using an appropriate time and pressure setting. Similarly, microdroplets of DMEM/F12 medium were injected with the OG-labeled dextran solution using the same time and pressure setting, and the microinjection pipette. After microinjection, fluorescence images of injected oocytes and microdroplets were captured using a Nikon TMD inverted microscope equipped with high pressure mercury arc lamb, fluorescein selective filter set, and a CCD camera. To minimize errors due to possible fluctuations in mercury arc lamb output, each fluorescence image was captured by averaging 64 frames. FIG. 18 depicts typical fluorescence images of oocytes captured after the microinjection as described above. The fluorescence intensity of captured images was measured on a small spot in the center of the cell or droplet using the Metamorph software package (Universal Imaging Co., West Chester, Pa.) on a personal computer. Next, a standard curve was generated using different concentrations of the OG-labeled dextran within the microdroplets (FIG. 19). The microinjected dextran concentrations in the oocytes and the microdroplets were estimated using the standard curve. Finally, injection volumes were calculated from the dextran concentrations found in microinjected oocytes and microdroplets. Evaluation of the injection volumes showed that injection into microdroplets reflects injection volumes into oocytes in a sensitivity of pL-range (FIG. 5).

As described earlier, another approach that was also used to determine the concentration of the injected sugar involved comparing the volume of an oocyte in hypertonic medium (i.e., 0.1 M trehalose) before and after microinjection. Because the contribution of 10 mM TRIS to the total osmolarity of the injection buffer (which typically also includes 800 or 1000 mM sugar) is negligible, the re-expansion of the shrunken oocytes in a 0.10 M sugar/medium mixture upon microinjection of sugar can be attributed to the introduction of sugar into the cells. Thus, the extent of the re-expansion after microinjection indicates the intracellular concentration of the injected sugar. Indeed, individual mouse oocytes showed similar volumetric response to the same amount of injected trehalose. Such an experiment is summarized in FIGS. 3B–3D which display a typical oocyte at an isotonic volume (FIG. 3B), a shrunken oocyte in hypertonic medium before microinjection of trehalose (FIG. 3C), and a re-expanded oocyte in hypertonic medium after microinjection of trehalose equal to the extra-cellular trehalose concentration (FIG. 3D).

To achieve a desired cytoplasmic concentration of sugar after microinjection and before any concentration of the intracellular sugar due to freezing or drying of the cell, either the volume of preservation agent that is injected into the cell, the initial concentration of the sugar in the preservation agent, or both can be adjusted. For example, to achieve a relatively high cytoplasmic concentration of sugar after microinjection, a relatively large volume of preservation agent may be injected or a relatively high concentration of sugar may be injected. Alternatively, if a lower cytoplasmic concentration of sugar is desired, the volume of preservation agent that is injected may be decreased, the concentration of the sugar in the preservation agent may be reduced, or both changes may be made. The volume of preservation agent that is injected may be chosen so that the volume is not so large that the resulting increase in the volume of the cytoplasm causes the cell to lyse. Additionally, the volume of preservation agent may be chosen so that it is not too small to be accurately measured and injected.

Similarly, to achieve a desired extracellular concentration of sugar after dilution into a liquid medium containing the cell, either the volume of preservation agent that is added to the medium, the initial concentration of the sugar in the preservation agent that is added to the medium, or both can be adjusted. Thus, the extracellular concentration of sugar may be increased by adding a larger volume or a more concentrated solution to the liquid medium. For a preservation agent that is added to a cell grown on a solid medium, such as agar, the desired extracellular sugar concentration can be achieved by contacting the cell with a preservation agent containing sugar at the desired concentration.

A bio-preservation agent useful in this process includes any chemical that has cryoprotective properties and is ordinarily non-permeable. In particular, the bio-preservation agent can include sugars either alone or mixed together with other traditional bio-preservation agents. Carbohydrate sugars such as trehalose, sucrose, fructose, and raffinose, may be microinjected to concentrations less than or equal to about 1.0 M, and more preferably, less than or equal to about 0.4 M. In another preferred embodiment, the concentration is between 0.05 and 0.20 M, inclusive. Additionally, an extracellular sugar (e.g., sucrose) or traditional bio-preservation agent (e.g., DMSO) may be added prior to storage. If the cells were incubated in a hypertonic solution prior to microinjection, the substantially non-permeable solute may be allowed to remain in the media after microinjection or may be removed from the media by washing the cells with media containing a lower concentration, or none, of this solute.

Certain sugars or polysaccharides which ordinarily do not permeate cell membranes because they are too large to pass through the membrane have superior physiochemical and biological properties for cryopreservation purposes. While these sugars ordinarily do not permeate cell membranes on their own, using the method of the invention, these ordinarily non-permeating sugars may be microinjected intracellularly to result in a beneficial effect.

Non-permeating sugars having a stabilizing or preserving effect on cells that are especially useful as the preservation agent in the present method include sucrose, trehalose, fructose, dextran, and raffinose. Among these sugars, trehalose, a non-reducing disaccharide of glucose, has been shown to be exceptionally effective in stabilizing cell structures at low concentrations. Trehalose is the most preferred sugar for use with the present method. It has an exceptional ability to stabilize and preserve proteins, viruses, and bacteria as well as an unusual ability to form stable glasses at high temperatures. Trehalose has physicochemical properties for use as an oocyte cell cryoprotective agent (CPA) that are far superior to traditional agents. Further, trehalose, contained in many food products, is relatively non-toxic and may allow for cryopreservation protocols which do not require CPA removal, resulting in an infusible end product. Sucrose, which has properties similar to those of trehalose and which is widely available and relatively inexpensive, may also be preferred for certain applications. There are also advantages to using dextran either alone or in combination with other sugars, such as trehalose or sucrose. Dextran has a very high glass transition temperature (Tg'), but does not have some of the advantages that are present in sucrose or trehalose, such as the ability to stabilize biological components. Thus, a dextran trehalose mixture, or dextran sucrose mixture, may have added benefits.

The addition of extracellular glycolipids or glycoproteins may also stabilize the cell membrane. While not meant to limit the invention to any particular theory, it is hypothesized that the sugar groups in glycolipids may hydrogen-bond with the hydrophilic head groups of membrane phospholipids, stabilizing the membrane against freezing-induced stress. Additionally, it is possible that the glycolipids may be incorporated into the lipid bilayer and increase the integrity of the membrane.

Following the microinjection of the preservation agent, the cells are prepared for storage (40). A variety of methods for freezing and/or drying may be employed to prepare the cells for storage. In particular, three approaches are described herein: vacuum or air drying (50), freeze drying (60), and freeze-thaw (70) protocols. Drying processes have the advantage that the stabilized biological material may be transported and stored at ambient temperatures.

Figure 6B:
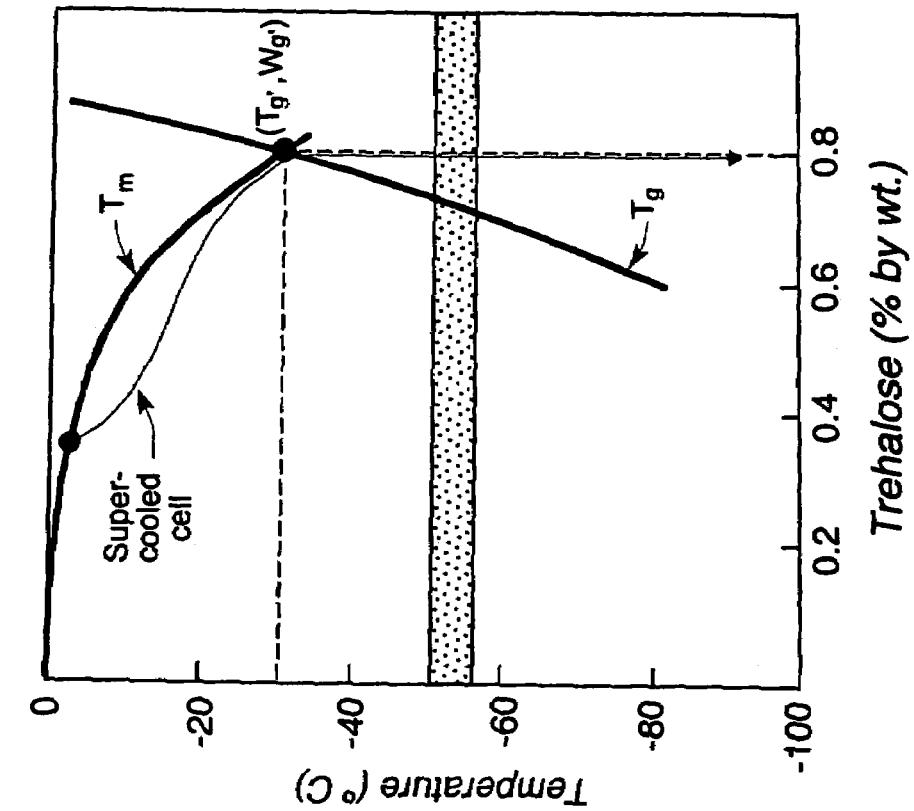
FIGS. 6A and 6B are phase diagrams of DMSO and trehalose.
Figure 6A:
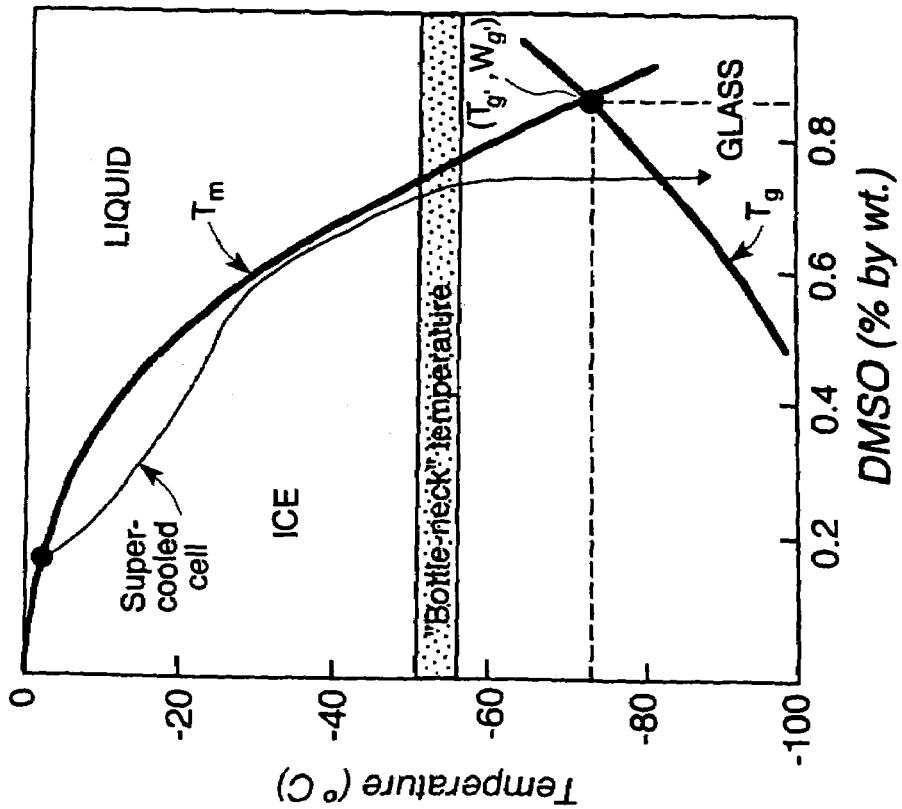

FIG. 6 shows a phase diagram of a conventional penetrating cryoprotectant (DMSO) versus a common sugar (trehalose). Typically, oocytes loaded with 1 to 2M DMSO are cooled at a very slow cooling rate (0.3 to 0.5° C./min) to an intermediate temperature (−60° C. to −80° C.) before plunging in liquid nitrogen for storage. As a result of the slow cooling rate, oocytes have ample time to dehydrate and closely follow the equilibrium melting curve (Tm) of the cryoprotectant solution (e.g., DMSO) down to a temperature range between −30° C. and −50° C. Since the permeability of the plasma membrane to water decreases exponentially as a function of decreasing temperature at temperatures below −50° C., the cellular dehydration becomes negligible for any practical purposes. As the temperature is further decreased to the storage temperature, the unfrozen solution inside the oocytes becomes more concentrated until the temperature reaches the Tg curve at the point Tg', and then the solution becomes glass. As a result, the fraction of the cellular water which remains in the cell, crystallizes during further cooling to the storage temperatures (typically below the glass transition temperature, Tg'). The formation of ice inside the cells is believed to result in cell death if the fraction of cellular water transformed to ice phase surpasses a certain limit (usually 5%). On the other hand, the phase diagram of trehalose is such that Tm and Tg curves cross each other at a very high subzero temperature (approximately −30° C.) compared to DMSO (approximately −80° C.). As a result, one can freeze the oocyte, and dehydrate very close to its glass transition temperature while the membrane water permeability is still high, and thereafter plunge in liquid nitrogen to vitrify the sample. The sample can then be stored at this temperature. This process enables oocytes to overcome the so-called "bottle-neck" effect observed below −50° C. with most conventional penetrating cryoprotectants. Beneficial results may also be obtained by applying extracellular sugars, in addition to the intracellular sugars, to the cell.

The suspended material can then be stored (90,100) at cryopreservation temperatures, for example, by leaving the vials in $LN_2$, for the desired amount of time. Preferably, the cells are stored at a temperature equal to or less than the Tg' of the cryoprotectant so that the cells remain in the glassy state. Preferred storage temperatures are at least 5, 10, 15, 20, 30, or 40° C. below the Tg'. The cells are also preferably maintained at a relatively constant temperature during storage. Preferably, the storage temperature changes by less than 20, 10, 5, or 3° C. during storage. The suspended cells can then be recovered from storage (110) by thawing (120) in a 37° C. water bath with continuous, mild agitation for 5 minutes.

Protocols for vacuum or air drying (50) and for freeze drying (60) proteins are well characterized in the art (Franks et al., "Materials Science and the Production of Shelf-Stable Biologicals," BioPharm, October 1991, p. 39; Shalaev et al., "Changes in the Physical State of Model Mixtures during Freezing and Drying: Impact on Product Quality," Cryobiol. 33, 14–26 (1996)) and such protocols may be used to prepare cell suspensions for storage with the method of the invention. In addition to air-drying, other convective drying methods that may be used to remove water from cell suspensions include the convective flow of nitrogen or other gases. In one preferred embodiment, the gas used for convective drying does not contain oxygen which may be deleterious to certain cells.

An exemplary evaporative vacuum drying protocol (130) useful with the method of the invention may include placing 20 μl each into wells on 12 well plates and vacuum drying for 2 hours at ambient temperature. Of course, other drying methods could be used, including drying the cells in vials. Cells prepared in this manner may be stored dry (140), and rehydrated (160) by diluting in DMEM or any other suitable media.

A method of the invention using freeze drying (60) to prepare the cells for storage (40) begins with freezing (80) the cell suspension. While prior art freezing methods may be employed, the simple plunge freezing method described herein for the freeze-thaw method may also be used for the freezing step (80) in the freeze drying protocol.

After freezing, a two stage drying process (150) may be employed. In the first stage, energy of sublimation is added to vaporize frozen water. When freeze drying cells, the primary criterion for selecting the temperature of the primary drying phase is that it must be below the glass phase transition temperature of the freeze concentrated solution to avoid collapse and undesirable chemical reactions. In general, the highest possible temperature that will not damage the sample should be used so that sublimation will occur quickly. Typically, the primary drying occurs at a constant temperature maintained below the glass transition temperature for the freeze concentrated solution.

Secondary drying is performed after the pure crystalline ice in the sample has been sublimated. Secondary drying cannot take place unless the temperature is raised above the glass phase transition temperature of the freeze concentrated solute, however, it is crucial that the sample temperature does not rise above the collapse temperature above which the specimen is believed to mechanically collapse due to viscous flow.

Freeze dried cells can be stored (140) and hydrated (160) in the same manner as described above for vacuum drying. Viable cells may then be recovered (170).

After the recovery of cells from a frozen or dried state, any external cyropreservation may be optionally removed from the culture media. For example, the media may be diluted by the addition of the corresponding media with a lower concentration of cyropreservation agent. For example, the recovered cells may be incubated for approximately five minutes in media containing a lower concentration of sugar than that used for cell storage. For this incubation, the media may contain the same sugar that was used as the cyropreservation agent; a different cryopreservation agent, such as galactose; or any other substantially non-permeable solute. To minimize any osmotic shock induced by the decrease in the osmolarity of the media, the concentration of the extracellular cyropreservation agent may be slowly decreased by performing this dilution step multiple times, each time with a lower concentration of cyropreservation agent (FIG. 2). These dilution steps may be repeated until there is no extracellular cyropreservation agent present or until the concentration of cyropreservation agent or the osmolarity of the media is reduced to a desired level.

For cells that divide relatively quickly, such as fibroblasts, the internal concentration of sugar quickly decreases as the sugar is divided between the mother and daughter cells. Thus, the internal osmolarity of the cells may decrease to a level close to that of a traditional isotonic media, enabling the recovered cells to be cultured in an isotonic media without significant swelling or adverse effects caused by a difference between the internal and external osmolarity of the cells.

For culturing recovered cells that do not divide or that divide slowly, such as oocytes, using a hypertonic media may prevent or reduce the swelling of the cells that might otherwise occur if they were returned to an isotonic media. Thus, a hypertonic media for the culturing of certain recovered cells was developed using a two-prong approach. First, a standard culture medium called HTF (human tubal fluid medium) was modified to minimize the concentration of electrolytes (see FIG. 7, components marked with down arrows) and to increase other nutrients and amino acids (see FIG. 7, components marked with up arrows). The osmolarity of this medium was determined using an osmometer.

Because the osmolarity of this medium was approximately 285 mosm, which is close to the normal internal osmolarity of cells, this medium is called modified HTF, isotonic. Second, the water content of the medium was reduced to equally increase the concentrations of each component to achieve a final osmolarity of 320 mosm. This medium is called modified HTF, hypertonic, (see FIG. 7, last column).

To test the ability of modified HTF, isotonic and hypertonic media to support the fertilization and development of oocytes, these medias were used to culture fresh mouse metaphase II oocytes that had not been cyropreserved. As illustrated in FIG. 8, control mouse oocytes without intracellular trehalose cultured in either modified HTF, isotonic or modified HTF, hypertonic media had a high frequency of fertilization (90%) and development to blastocyst-stage (over 85%). Mouse oocytes injected with 0.07M trehalose also showed a high frequency of fertilization and blastocyst development in modified HTF, hypertonic media. At an intracellular trehalose of 0.15 M, the frequencies of fertilization and blastocyte formation were reduced, but still significant.

In subsequent experiments, the osmolality of the modified HTF, hypertonic 320 medium was further modified to 340 and 360 mOsm by raising the intracellular trehalose concentration to 0.15 and 0.20 M, respectively. FIG. 20 is a table listing the components of the modified hypertonic HTF media with 320, 340, and 360 mosm.

Zygotes were microinjected with 0.10, 0.15, and 0.20 M trehalose, and then cultured in the hypermedium with an osmolality of 320, 340, and 360 mOsm, respectively. Controls included untreated zygotes and zygotes exposed to 0.1 M extracellular trehalose for the duration of microinjection procedure. The zygotes in both control groups were cultured in the hypermedium (320 mOsm). The blastocyst rates for each experiment were calculated as a percentage of the two-cell embryos.

Figure 21:
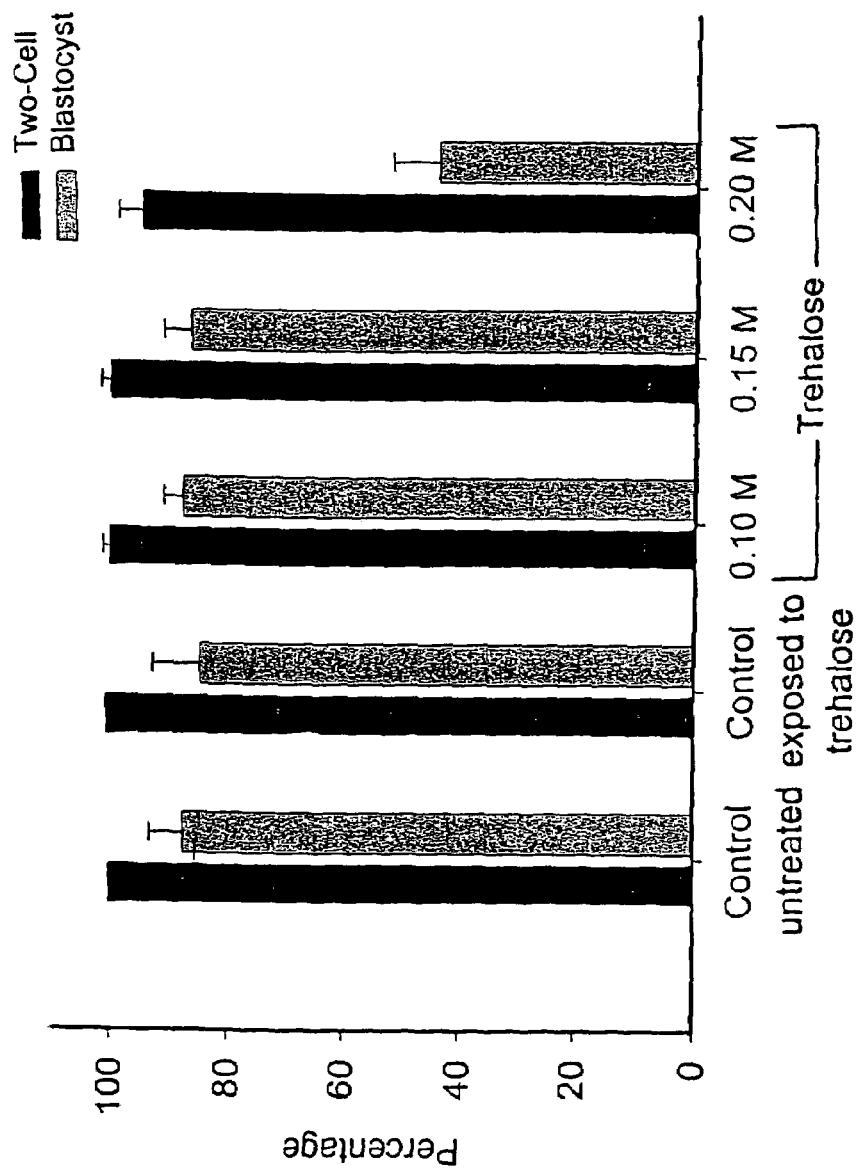
FIG. 21 is a graph summarizing the embryonic development of zygotes as a function of intracellular trehalose concentrations.

FIG. 21 shows the blastocyst formation rate as a function of intracellular trehalose concentrations. The data represent the mean±s.e.m of four to seven experiments. The blastocyst formation rate of zygotes microinjected with 0.2 M trehalose was significantly lower than that of other groups. Microinjection of 0.2 M trehalose also led to a greater imbalance between intra- and extracellular osmolality as compared to microinjection of 0.10 M or 0.15 M trehalose. Although the osmolality of the hypermedium increased to 360 mOsm upon microinjection of 0.20 M trehalose, this was not proportional to the increase in intracellular osmolality (80 mOsm vs. 200 mOsm). As a result, the zygotes experienced increased swelling and osmotic stress.

If desired, the composition and hypertonicity of the culture medium may be further optimized to increase the number of blastocysts or viable offspring that are formed. For example, a culture medium having a higher osmolarity (such as 330, 340, 350, 360, 370, or 380 mosm) may better mimic oviductal fluid (which may have an osmolarity of at least 360 mosm) and thus further promote development of viable offspring (Van Winkle et al., J. Expt Zool. 253: 215–219, 1990). Any other suitable hypertonic media with an osmolarity of at least 300, 310, 320, 330, 340, 350, 360, 370, 380, or more mosm may be used in preferred methods for culturing cells in vitro. These methods may be used to culture cells with or without intracellular sugar. These preferred media may also be used before, during, or after storage of cryopreserved cells.

Figure 9A:
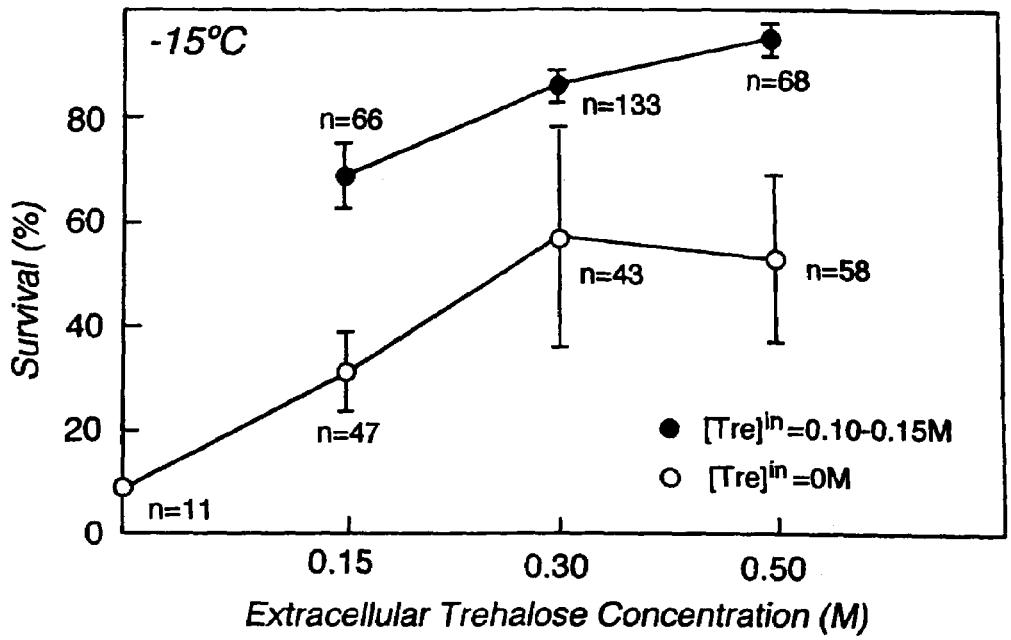
FIGS. 9A and 9B are a set of graphs showing the percent survival for metaphase II mouse oocytes with 0 or 0.10–0.15 M intracellular trehalose in the presence of various concentrations of extracellular trehalose.
Figure 9B:
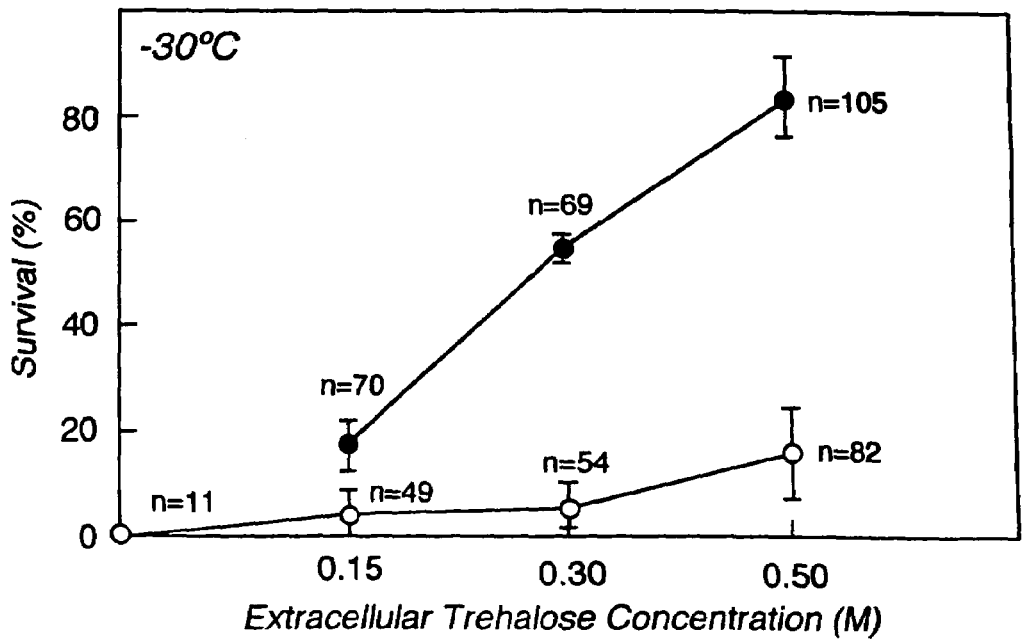

FIGS. 9A and 9B are a set of graphs showing the survival of cooled metaphase II mouse oocytes after overnight culture in modified HTF, hypertonic media as a function of extracellular trehalose concentration at −15° and −30° C., respectively. These experiments were performed using a cooling rate of 1° C./min, with or without approximately 0.10 to 0.15 M intracellular trehalose. Cell viability was assessed using the live/dead assay described herein. Additionally, light microscopy was used to visually determine whether the viable oocytes had an intact membrane and lacked signs of degeneration and fragmentation. At both −15 and −30° C., the addition of approximately 0.10 to 0.15 M trehalose inside oocytes dramatically increased the survival rate. Furthermore, at −30° C., the absence of internal trehalose resulted in few viable oocytes after freezing. The amount of extracellular trehalose had a dramatic, dose-dependent effect on survival. As the extracellular amount of trehalose in the freezing solution was increased from 0.15 M (approximately the same amount as the intracellular trehalose) to 0.30 M or 0.50 M, the survival rate improved from about 18, to 55 or 85%, respectively. This result shows the benefit of using both internal and external cryopreservation agents during cooling of cells.

Figure 10:
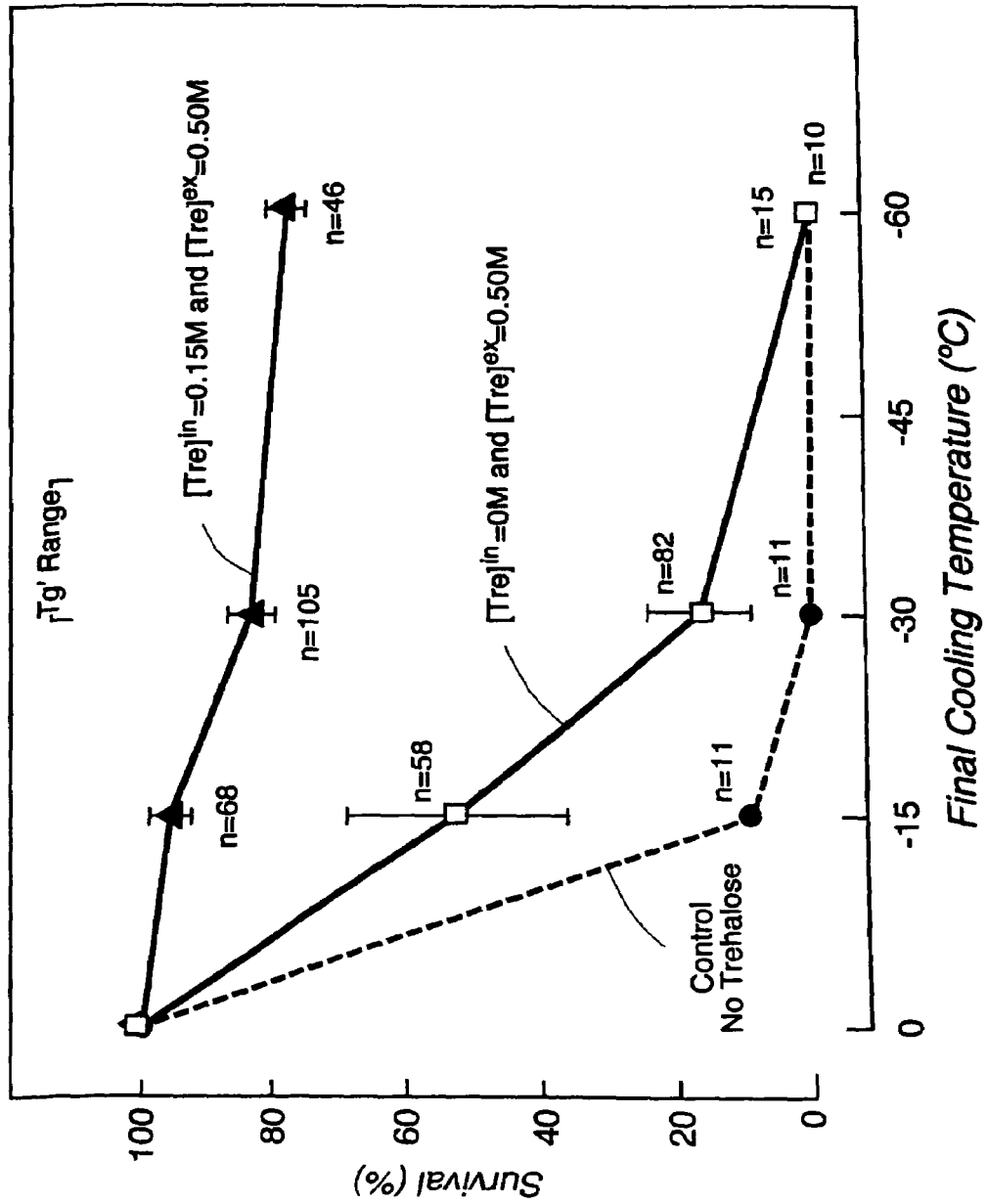
FIG. 10 shows the survival of cooled metaphase II mouse oocytes after overnight culture
Figure 11:
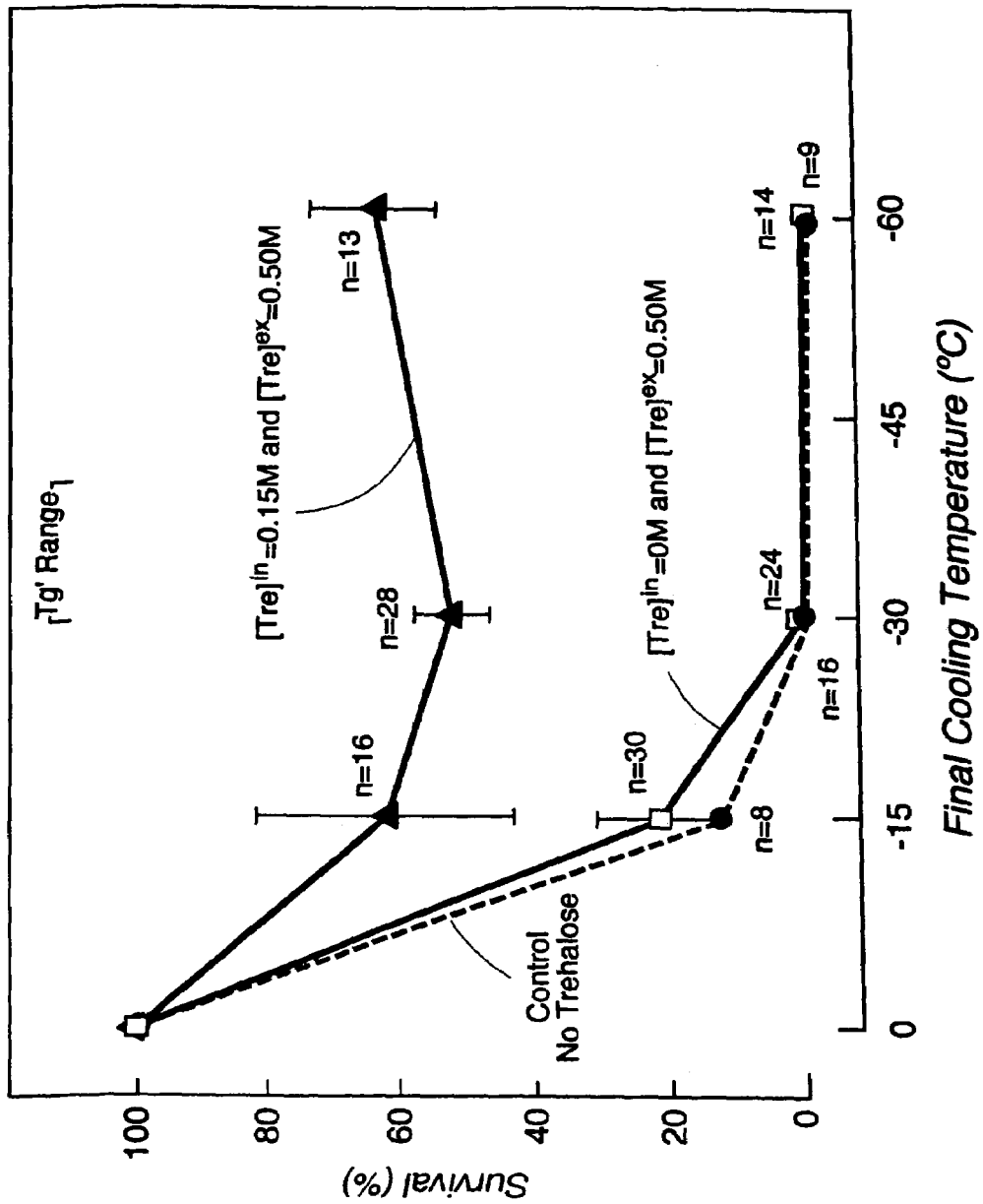
FIG. 11 shows the survival of cooled human oocytes after overnight culture.

FIG. 10 shows the survival of cooled metaphase II mouse oocytes after overnight culture in modified HTF media, isotonic. FIG. 11 shows the survival of cooled human oocytes after overnight culture in HTF media plus 0.1 M extracelluar trehalose. Cell survival was measured using the live/dead assay. Light microscopy was also used to visually determine whether the viable oocytes had an intact membrane and lacked signs of degeneration and fragmentation. The bracket labeled Tg' in FIG. 10 and FIG. 11 shows possible long-term storage temperatures when trehalose is present both intra- and extracellularly. In FIG. 10, oocytes were cooled at a very slow cooling rate to an intermediate temperature (−60° C.). Oocytes with no trehalose resulted in a 0% survival rate. Oocytes loaded with 0.50 M extracellular trehalose experienced some improvement over the control, but suffered a steady decrease in the survival rate as the temperature decreased. Oocytes loaded with 0.15 M intracellular and 0.50 M extracellular trehalose, on the other hand, maintained a survival rate between 80 and 100%. In comparison with the control and with oocytes in an extracellular trehalose solution, oocytes containing intracellular trehalose experienced a significant increase in survival rate.

Figure 12A:
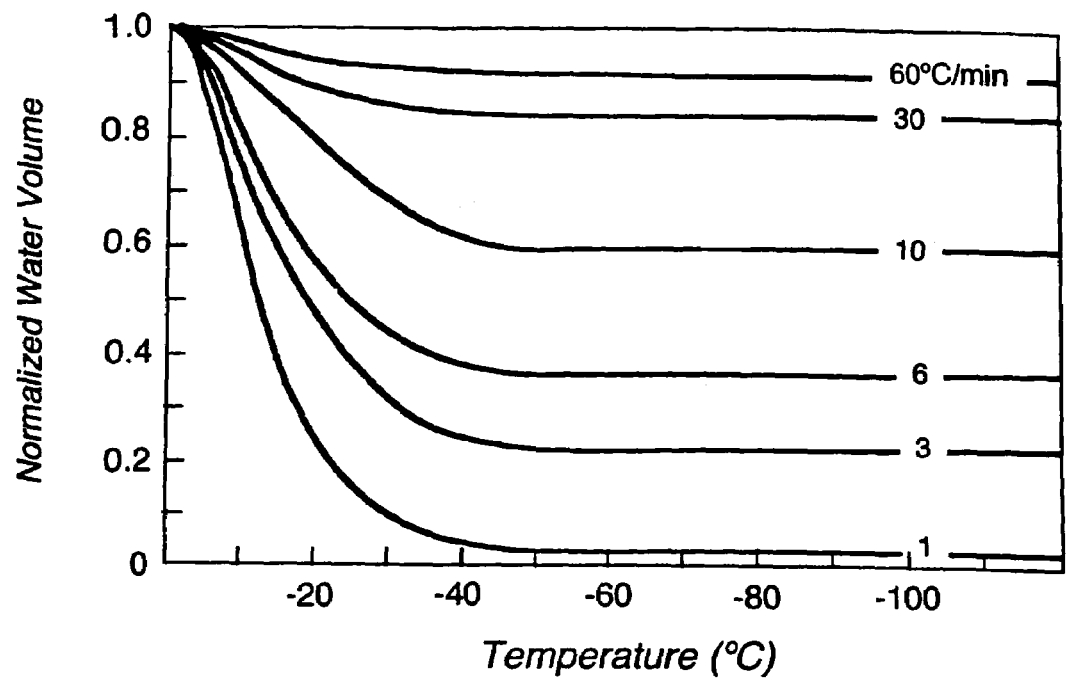
FIG. 12A is a graph of a set of curves showing the normalized water volume in oocytes as a function of temperature for different cooling rates.

FIG. 12A is a graph with multiple curves that illustrate the water content of mouse oocytes as a function of temperature for different cooling rates, based on the following well-established equations for the rate of water transport during freezing (Karlsson et al., Human Reproduction 11:1296–1305, 1996; Toner et al., J. of Membrane Biology 115:261–272, 1990).

$$\frac{dV}{dT} = \frac{LpRT}{Bv_w} A(\ln a_w^{ex} - \ln a_w^{in})$$

where R is the gas constant; T is the temperature; B is the cooling rate; $v_w$ is the partial molar volume of water, and $a_w^{ex}$ and $a_w^{in}$ are the water activities in the external and intracellular solutions, respectively. Lp is the water permeability given by $$Lp = Lpg \exp\left[-\frac{ELp}{R}\left(\frac{1}{T} - \frac{1}{T_R}\right)\right]$$

where Lpg is the reference water permeability at $T_R$; ELp is the activation energy or temperature dependence of water permeability, and $T_R$ is the reference temperature (typically, 0° C.).

As illustrated in these curves, the extent of dehydration of oocytes depends on the cooling rate. For example, very slow cooling rates may result in excess dehydration of oocytes. Alternatively, very fast cooling rates (e.g., 30 or 60° C./min), may result in minimal dehydration. Thus, intermediate cooling rates, such as those between 0.1 and 5° C./min, are preferable. For these rates, the water transport model predicts that the intracellular water volume will initially decrease and then asymptotically approach a constant value. As illustrated in this figure, water permeability is an exponential function of temperature with an activation energy, ELp, of 14.5 kcal/mol for mouse oocytes. Thus, as the temperature is lowered during freezing, Lp decreases precipitously and reaches almost zero for temperatures below −50° C./min. Due to the similarities between the temperature dependence of Lp (i.e., the value of ELp) for mouse oocytes and oocytes from other mammals, such as rats, bovine, and humans, similar dehydration behavior is expected for other oocytes. For example, ELp is 14.70 kcal/mol for human oocytes, compared to 14.5 kcal/mol for mouse oocytes (Paynter et al., Human Reproduction 14: 2338–2342, 1999).

Figure 12B:
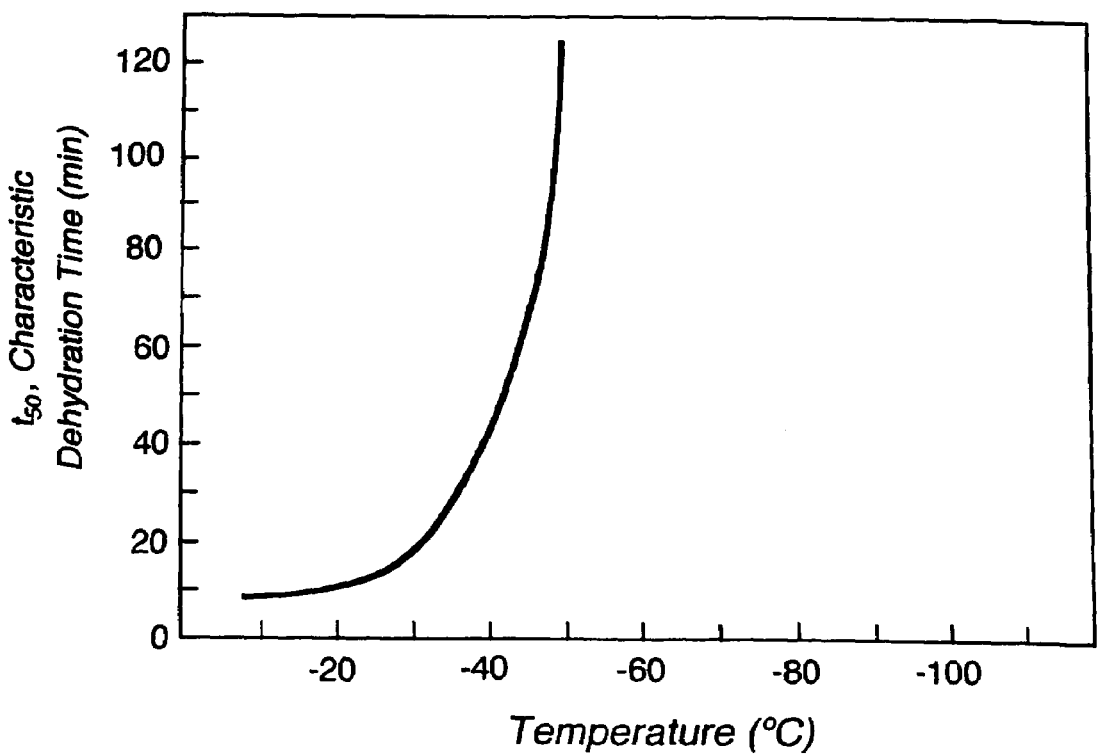
FIG. 12B is a graph showing the calculated dehydration time as a function of temperature. The dehydration time is defined as the time necessary for an oocyte to shrink in volume by 50% at a given temperature.

FIG. 12B is a graph that illustrates the calculated dehydration time necessary for the volume of an oocyte to be reduced by 50% at a given temperature. This graph was generated using the water transport equations listed above and clearly indicates that water transport is significantly reduced at low temperatures, especially at temperatures below −50° C. Thus, cells are preferably cooled using the methods of the invention to a final temperature of at least −50, −40, −30, −20, or −10° C. to allow dehydration to continue at a significant rate. After dehydration is complete, the cells may be stored at this temperature or at a lower temperature to maintain the cells in a glass state until they are needed.

Figure 13:
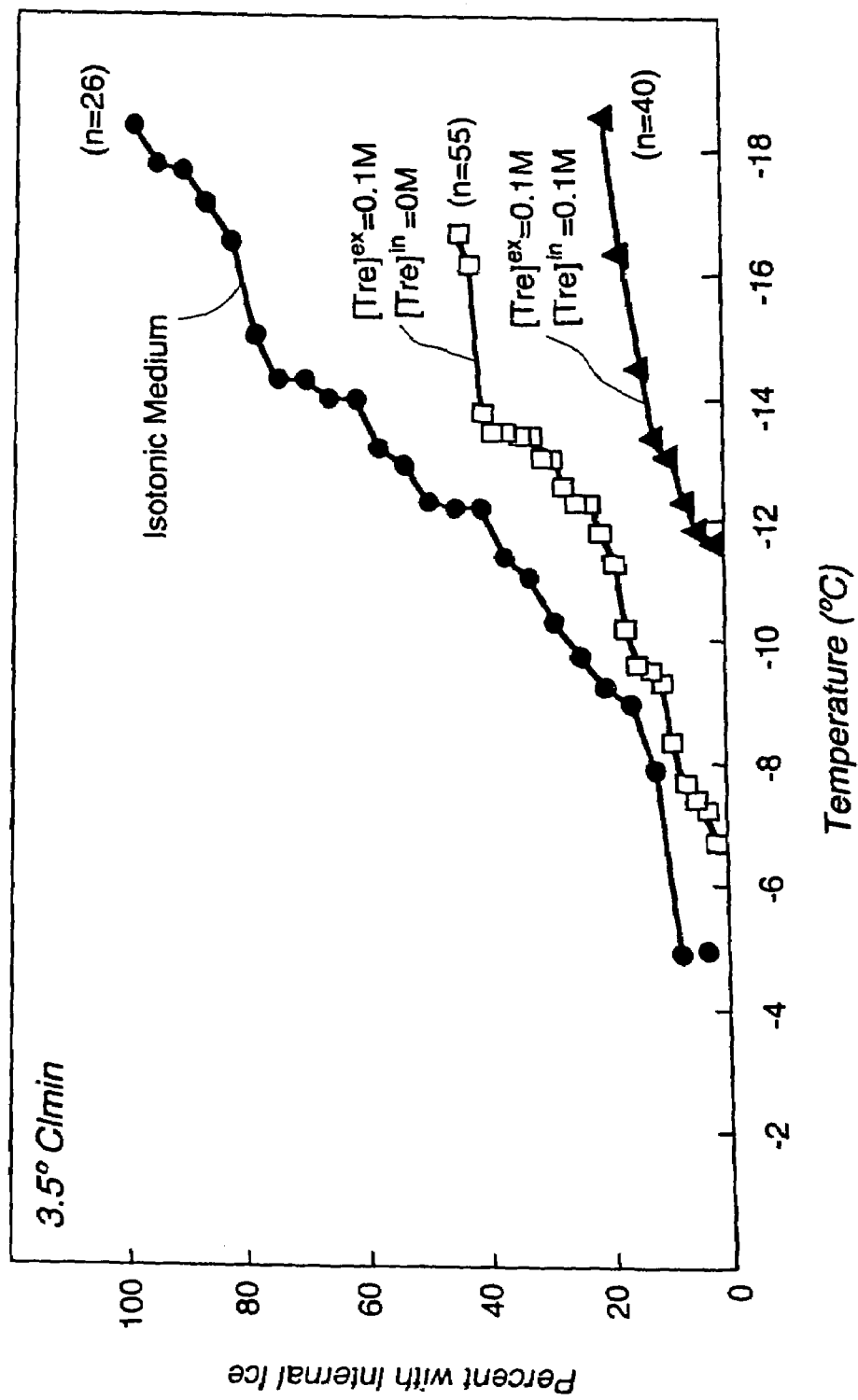
FIG. 13 is graph of a set of curves showing the cumulative incidence of intracellular ice as a function of temperature in the presence and absence of preservation agents.

FIG. 13 is a graph with a set of curves showing the percentage of oocytes that have intracellular ice at various temperatures. For this assay, standard cryomicroscopy procedures were used to cool oocytes at a rate of 3.5° C./min (Cosman et al., Cryo-Letters 10:17–38, 1989). The oocytes were observed using a cryomicroscope to determine whether intracellular ice had formed. The presence of intracellular ice was easily detected based on the black color that appeared due to the light scattered by the ice crystals. This assay was used to test control oocytes incubated in isotonic media alone, oocytes incubated in media with 0.1 M extracellular trehalose, and oocytes injected with 0.1 M trehalose and incubated in media with 0.1 M extracellular trehalose. As illustrated in FIG. 13, extracellular trehalose reduced the incidence of intracellular ice formation in oocytes. The frequency of intracellular ice was further reduced by the presence of intracellular trehalose in addition to the extracellular trehalose. If desired, the amount of intracellular ice may be further reduced by increasing the concentration of intracellular or extracellular sugar that is used. The ability of trehalose to significantly reduce internal ice allows faster cooling rates. In the field of cryobiology, it has been established that the faster the cooling rate without formation of lethal intracellular ice, the greater the chance of cell survival.

FIG. 14 is a table that lists sugars with a glass transition temperature of greater than −55° C. As illustrated in this table, sugars with higher molecular weights tend to have higher glass transition temperatures. Linear polymers also tend to have higher glass transition temperatures than branched polymers of the same molecular weight. Comparing linear and cyclic α-(1→4)-linked glucose hexamers, a cyclic oligomer (cyclodextrin, Tg'=−9° C.) had a higher glass transition temperature than a linear oligomer (maltohexaose, Tg'=−14.5° C.) (Levine and Slade, supra).

Figure 15:
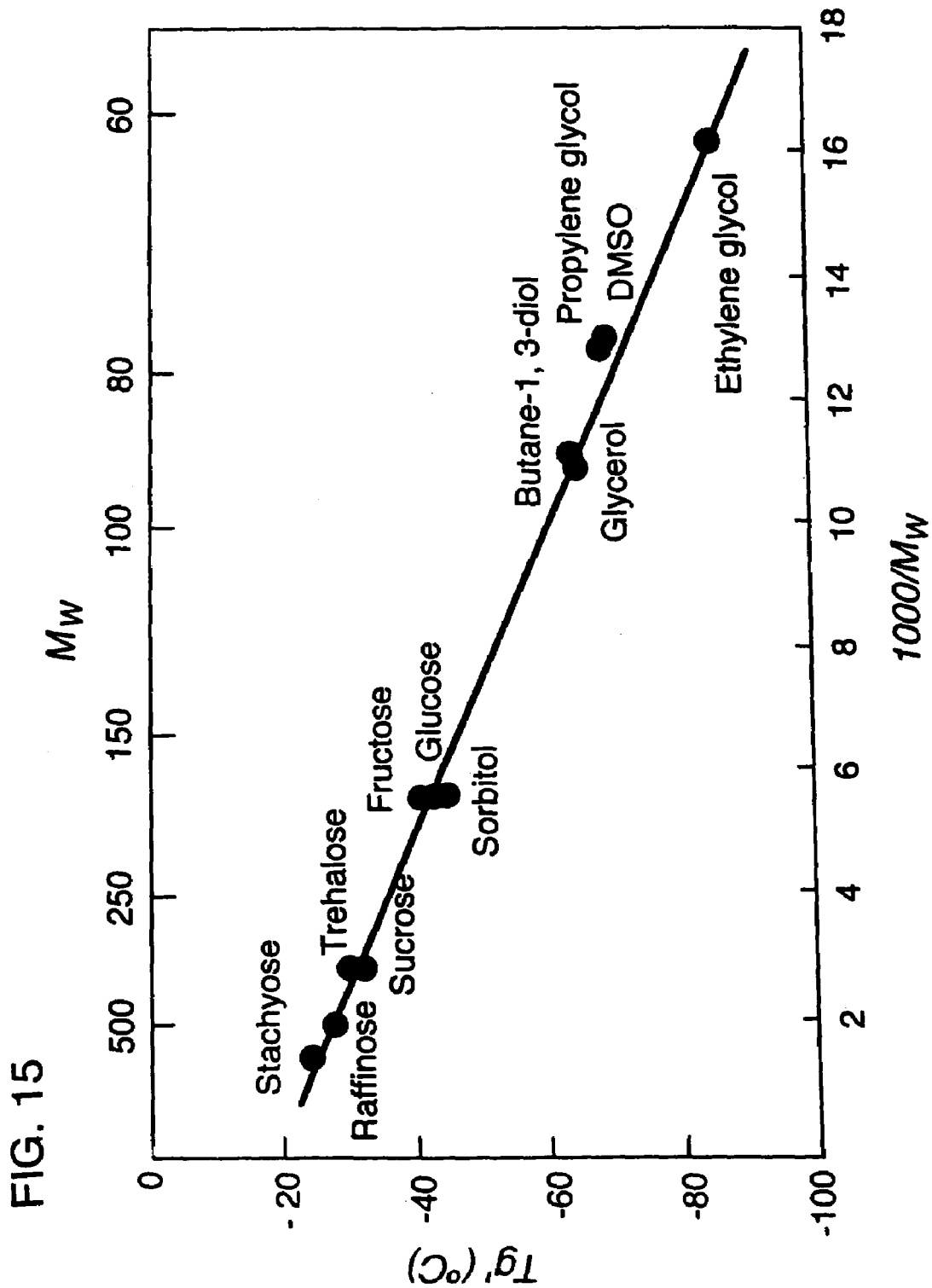
FIG. 15 is a graph showing the monotonic relationship between Tg' and molecular weight of several sugars and traditional cryoprotectants.

A graph of Tg' as a function of molecular weight for some sugars and traditional cryoprotectants is shown in FIG. 15. In a more comprehensive figure in Levine and Slade (supra) for 84 small sugars, the monotonic relationship between increasing Tg' and molecular weight yielded a linear correlation of r=−0.93. Thus, for sugars with a molecular weight of at least 120 daltons, their Tg' is at least −50° C.

OTHER EMBODIMENTS

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference.

What is claimed is:

1. A method of culturing an oocyte in vitro, comprising microinjecting into the cytoplasm of said oocyte a protective agent which (i) comprises a sugar, and (ii) is substantially non-permeating with respect to mammalian cell membranes and incubating said oocyte in a hypertonic medium having an osmolarity greater than 300 mosm.

2. The method of claim 1, wherein said protective agent comprises at least one sugar selected from the group consisting of sucrose, trehalose, fructose, dextran, and raffinose.

3. The method of claim 1, wherein said protective agent comprises at least one sugar selected from the group consisting of glucose, sorbitol, mannitol, lactose, maltose, and stachyose.

4. The method of claim 1, wherein said protective agent comprises at least one sugar with a glass transition temperature greater than −50° C.

5. The method of claim 4, wherein said protective agent comprises at least one sugar with a glass transition temperature greater than −30° C.

6. The method of claim 1, wherein said protective agent comprises at least one sugar with a molecular weight greater than 120 daltons.

7. The method of claim 1, wherein said protective agent comprises a glycolipid or a glycoprotein that comprises at least one sugar moiety derived from a sugar with a glass transition temperature greater than −50° C.

8. The method of claim 1, wherein the cytoplasmic concentration of said sugar is less than or equal to about 1.0 M following microinjection.

9. The method of claim 1, wherein the cytoplasmic concentration of said sugar is less than or equal to about 0.2 M following microinjection.

10. A method of culturing an embryo in vitro comprising microinjecting into the cytoplasm of said embryo a protective agent which (i) comprises a sugar, and (ii) is substantially non-permeating with respect to mammalian cell membranes and incubating said embryo in a hypertonic medium having an osmolarity greater than 300 mosm.

11. The method of claim 10, wherein said protective agent comprises at least one sugar selected from the group consisting of sucrose, trehalose, fructose, dextran, and raffinose.

12. The method of claim 10, wherein said protective agent comprises at least one sugar selected from the group consisting of glucose, sorbitol, mannitol, lactose, maltose, and stachyose.

13. The method of claim 10, wherein said protective agent comprises at least one sugar with a glass transition temperature greater than −50° C.

14. The method of claim 10, wherein said protective agent comprises at least one sugar with a glass transition temperature greater than −30° C.

15. The method of claim 10, wherein said protective agent comprises at least one sugar with a molecular weight greater than 120 daltons.

16. The method of claim 10, wherein said protective agent comprises a glycolipid or a glycoprotein that comprises at least one sugar moiety derived from a sugar with a glass transition temperature greater than −50° C.

17. The method of claim 10, wherein the cytoplasmic concentration of said sugar is less than or equal to about 1.0 M following microinjection.

18. The method of claim 10, wherein the cytoplasmic concentration of said sugar is less than or equal to about 0.2 M following microinjection.

19. The method of claim 1, wherein the osmolarity of said medium is greater than 320 mosm.

20. The method of claim 19, wherein the osmolarity of said medium is greater than 340 mosm.

21. The method of claim 20, wherein the osmolartiy of said medium is greater than 360 mosm.

22. The method of claim 1, wherein said medium comprises a sugar selected from the group consisting of sucrose, trehalose, fructose, dextran, and raffinose.

23. The method of claim 10, wherein the osmolarity of said medium is greater than 320 mosm.

24. The method of claim 23, wherein the osmolarity of said medium is greater than 340 mosm.

25. The method of claim 24, wherein the osmolartiy of said medium is greater than 360 mosm.

26. The method of claim 10, wherein said medium comprises a sugar selected from the group consisting of sucrose, trehalose, fructose, dextran, and raffinose.

* * * * *

UNITED STATES PATENT AND TRADEMARK OFFICE
CERTIFICATE OF CORRECTION

PATENT NO. : 7,094,601 B2
APPLICATION NO. : 10/749369
DATED : August 22, 2006
INVENTOR(S) : Toner et al.

It is certified that error appears in the above-identified patent and that said Letters Patent is hereby corrected as shown below:

On the Title Page, in References Cited, in OTHER PUBLICAITONS, in Shanina et al.,
  replace "Comparision" with --Comparison--;
  in Guo et al., replace "desicccation" with --desiccation--;
  pg 2, col. 2, in Bell et al., replace "Constrast" with --contrast--;
  pg 2, col. 2, in Bell et al., replace "*Investigavtive*" with --*Investigative*--.

Column 2, Line 64, replace "monolayers" with --monolayer--.

Column 3,
  Line 33, replace "cyropreservation" with --cryopreservation--;
  Line 35, replace "cyropreservation" with --cryopreservation--;
  Line 54, replace "cyropreservation" with --cryopreservation--;

Column 5, Line 1, replace "FIGSA." with --FIGS.--;
  Line 48, replace "cyropreservation" with --cryopreservation--.

Column 10,
  Line 28, replace "cyropreservation" with --cryopreservation--;
  Line 31, replace "cyropreservation" with --cryopreservation--;
  Line 42, replace "cyropreservation" with --cryopreservation--;
  Line 44, replace "cyropreservation" with --cryopreservation--;
  Line 45, replace "cyropreservation" with --cryopreservation--;

Column 11, Line 11, replace "cyropreserved" with --cryopreserved--.

UNITED STATES PATENT AND TRADEMARK OFFICE
CERTIFICATE OF CORRECTION

PATENT NO.       : 7,094,601 B2
APPLICATION NO.  : 10/749369
DATED            : August 22, 2006
INVENTOR(S)      : Toner et al.

It is certified that error appears in the above-identified patent and that said Letters Patent is hereby corrected as shown below:

Column 16,
    Line 8, replace "osmolartiy" with --osmolarity--;
    Line 17, replace "osmolartiy" with --osmolarity--.

Signed and Sealed this

Sixth Day of February, 2007

JON W. DUDAS
*Director of the United States Patent and Trademark Office*